(12) United States Patent
Memic et al.

(10) Patent No.: US 11,628,069 B2
(45) Date of Patent: Apr. 18, 2023

(54) 3D PRINTING OF POLYMERIC BIOCERAMICS FOR THE TREATMENT OF BONE DEFECTS

(71) Applicants: King Abdulaziz University, Jeddah (SA); NUtech Ventures, Lincoln, NE (US)

(72) Inventors: Adnan Memic, Jeddah (SA); Tuerdimaimaiti Abudula, Jeddah (SA); Ali Tamayol, Lincoln, NE (US); Azadeh Mostafavi, Lincoln, NE (US); Carina Russell, Lincoln, NE (US); Tyrell Williams, Lincoln, NE (US); Numan Abdullah Salah, Jeddah (SA); Ahmed Salem AlShahrie, Jeddah (SA); Ammar AbdulGhani Melaibari, Jeddah (SA); Asija Memic, Jeddah (SA); Mohammed Shaaban Abdelwahab, Jeddah (SA); Mehdi Kazemzadeh Narbat, Lincoln, NE (US)

(73) Assignees: KING ABDULAZIZ UNIVERSITY, Jeddah (SA); BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 17/564,417

(22) Filed: Dec. 29, 2021

(65) Prior Publication Data
US 2022/0202591 A1 Jun. 30, 2022

Related U.S. Application Data

(60) Provisional application No. 63/131,345, filed on Dec. 29, 2020.

(51) Int. Cl.
*A61F 2/46* (2006.01)
*B29C 64/10* (2017.01)
(Continued)

(52) U.S. Cl.
CPC .......... *A61F 2/4601* (2013.01); *A61F 2/2846* (2013.01); *A61F 2/2875* (2013.01);
(Continued)

(58) Field of Classification Search
CPC .......................... A61F 2/4601; B29C 64/118
See application file for complete search history.

(56) References Cited

U.S. PATENT DOCUMENTS

| 5,556,429 A * | 9/1996 | Felt | A61F 2/30756 606/92 |
| 10,888,428 B2 * | 1/2021 | Hoelzle | B33Y 30/00 |

(Continued)

FOREIGN PATENT DOCUMENTS

EP 2351590 A2 * 8/2011 ........ A61M 5/14546

OTHER PUBLICATIONS

Bella et al. In situ handheld three-dimensional bioprinting for cartilage regeneration. J Tissue Eng Regen Med. Mar. 2018;12(3):611-621. (Year: 2018).*

(Continued)

*Primary Examiner* — Cachet I Proctor
(74) *Attorney, Agent, or Firm* — WCF IP

(57) ABSTRACT

A filament or printing material placed in a syringe for 3D printing comprising polymers, proteins, and/or functional particles and materials is provided. Methods of treating a bone defect in a subject in need thereof comprising using a handheld 3D printer to apply a filament or the printing material placed in a syringe to the bone defect of the subject are also provided. Methods of fixing or gluing natural or synthetic bone grafts using a handheld 3D printer to apply a (Continued)

filament or the printing material placed in a syringe over and around the defect or at the interface of a flap and the bone. Methods of printing a graft cage for retaining bone grafts and/or bone graft substitute in its desired location during healing for treatment of critical-sized segmental defects in long bones are provided.

18 Claims, 14 Drawing Sheets

(51) Int. Cl.
| | |
|---|---|
| A61L 27/46 | (2006.01) |
| A61L 27/38 | (2006.01) |
| A61F 2/28 | (2006.01) |
| B29C 64/118 | (2017.01) |
| B33Y 80/00 | (2015.01) |
| B33Y 70/00 | (2020.01) |
| B33Y 10/00 | (2015.01) |
| B29L 31/00 | (2006.01) |

(52) U.S. Cl.
CPC ....... *A61L 27/3834* (2013.01); *A61L 27/3847* (2013.01); *A61L 27/46* (2013.01); *B29C 64/118* (2017.08); *B33Y 10/00* (2014.12); *B33Y 70/00* (2014.12); *B33Y 80/00* (2014.12); *A61F 2002/285* (2013.01); *A61F 2002/2835* (2013.01); *A61F 2002/465* (2013.01); *A61F 2002/469* (2013.01); *A61L 2300/404* (2013.01); *A61L 2400/06* (2013.01); *A61L 2400/12* (2013.01); *A61L 2430/02* (2013.01); *B29L 2031/7532* (2013.01)

(56) References Cited

U.S. PATENT DOCUMENTS

| | | | | |
|---|---|---|---|---|
| 2016/0287391 | A1* | 10/2016 | Larsen | A61F 2/30907 |
| 2016/0368211 | A1* | 12/2016 | Tran | A61L 27/3834 |
| 2016/0374770 | A1* | 12/2016 | Janik | A61B 34/20 |
| | | | | 604/500 |
| 2017/0198252 | A1 | 7/2017 | Mironov et al. | |
| 2019/0076251 | A1* | 3/2019 | Daniel | A61F 2/2846 |
| 2019/0134902 | A1* | 5/2019 | Jiang | A61L 27/38 |
| 2020/0030491 | A1* | 1/2020 | Weisman | B33Y 40/00 |
| 2020/0123485 | A1* | 4/2020 | Tamayol | C12N 5/0062 |
| 2021/0007778 | A1* | 1/2021 | Shoham | A61B 34/77 |
| 2021/0031449 | A1* | 2/2021 | Belcher | B33Y 10/00 |
| 2022/0031460 | A1* | 2/2022 | Gotz | A61F 2/2875 |
| 2022/0202591 | A1 | 6/2022 | Memic et al. | |

OTHER PUBLICATIONS

Scott. The BioPen: 3D Bioprinting Pen Lets Surgeons Draw New Cells Directly Onto Bone . 3Dprint.com. Apr. 2016. retrieved from https://3dprint.com/127916/biopen-3d-bioprinting-pen/ (Year: 2016).*

Shitole et al. Electrospun polycaprolactone/hydroxyapatite/ZnO nanofibers as potential biomaterials for bone tissue regeneration. Mater Sci: Mater Med 30, 51 (2019) (Year: 2019).*

Shim et al. Bioprinting of a mechanically enhanced three-dimensional dual cell-laden construct for osteochondral tissue engineering using a multi-head tissue/organ building system. Journal of Micromechanics and Microengineering, vol. 22, No. 8. Jul. 2012 (Year: 2012).*

Doyle et al. Melt electrospinning writing as reinforcement scaffolds of biofabricated articular human cartilage. May 2018. Retrieved from https://www.researchgate.net/publication/331729640_Melt_electrospinning_writing_as_reinforcement_scaffolds_of_biofabricated_articular_human_cartilage (Year: 2018).*

Wang et al. The trend towards in vivo bioprinting. International Journal of Bioprinting vol. 5, Issue 1 (2015) (Year: 2015).*

Cho et al. Evaluation of the antibacterial activity and cell response for 3D printed polycaprolactone/nanohydroxyapatite scaffold with zinc oxide coating. Polymers vol. 12. 2020 (Year: 2020).*

Cho, Y. et al., "Evaluation of the Antibacterial Activity and Cell Response for 3d-Printed Polycaprolactone/Nanohydroxyapatite Scaffold with Zinc Oxide Coating", Polymers vol. 12, 2020.

* cited by examiner

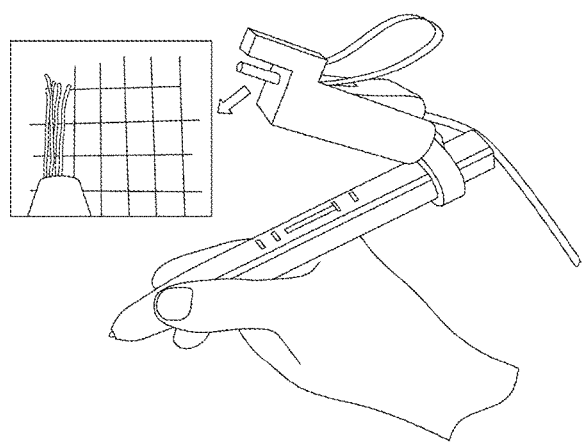
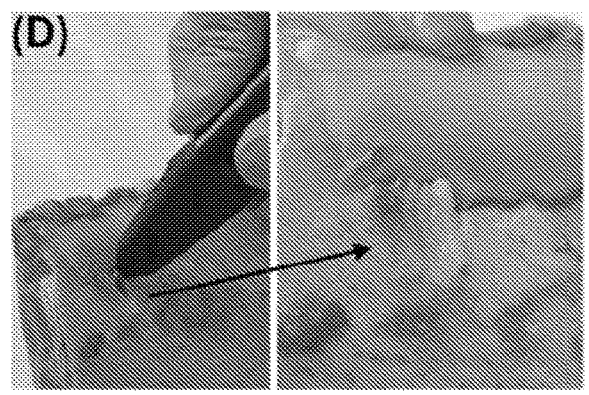
FIG. 4C
FIG. 4D
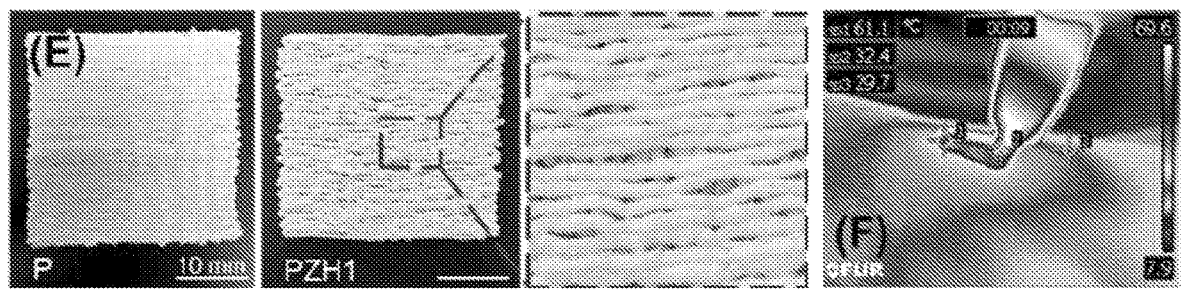
FIG. 4E
FIG. 4F

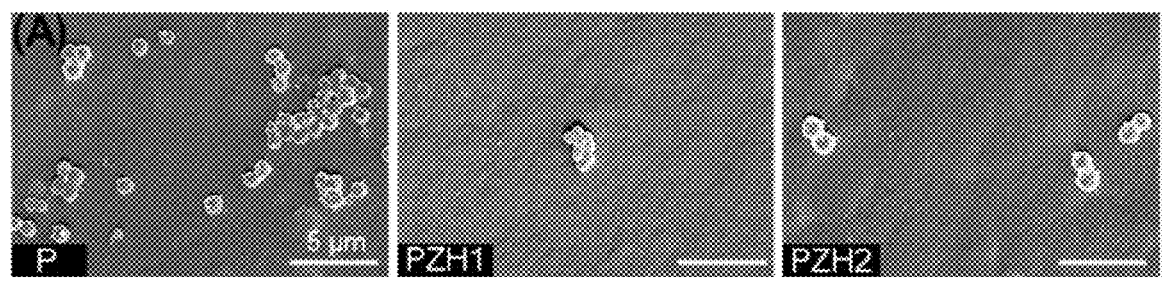
FIG. 5A
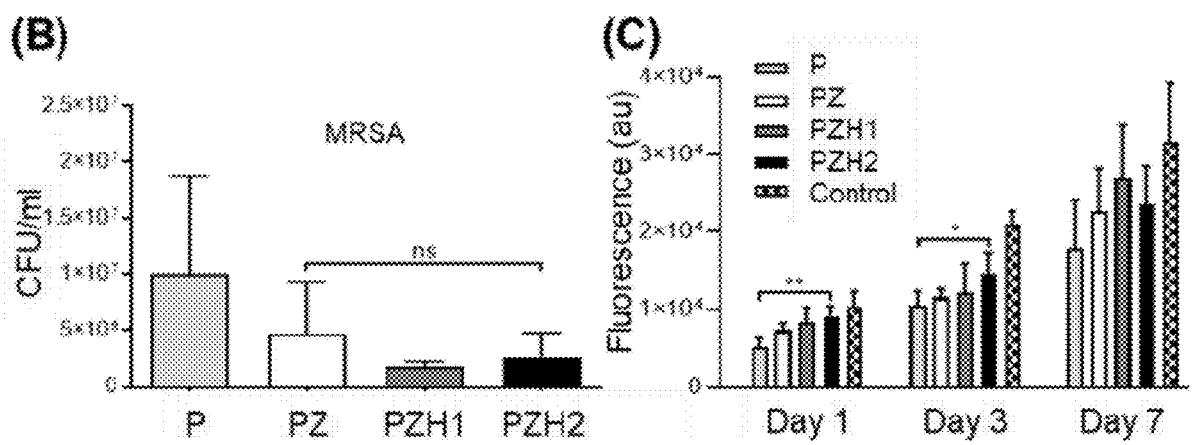
FIG. 5B
FIG. 5C

3D PRINTING OF POLYMERIC BIOCERAMICS FOR THE TREATMENT OF BONE DEFECTS

CROSS-REFERENCE TO RELATED APPLICATIONS

This application claims the benefit of U.S. Provisional Application 63/131,345 filed Dec. 29, 2020, the complete contents of which are incorporated herein by reference.

FIELD OF THE INVENTION

The invention is generally related to heat flowable absorbable, biodegradable filaments/printing material intended for treating bone defects as bone void filler or for fixing/adhering bone fractures, or other bone grafts, or for retaining bone grafts or bone graft substitute in its desired location during healing in situ by direct application using a handheld three-dimensional (3D) printer. The subject invention may be used in neurosurgical craniotomies, cranio-maxillofacial (CMF) surgery reconstruction such as CMF trauma, mandibular reconstruction, orthopedic surgery, facial fractures trauma, spine, and extremities such as hand surgery. The subject invention may also be used in conjunction with other synthetic, autograft, allograft, and xenograft bone grafts or bone void fillers. The subject invention can replace fracture fixation devices in no-load bearing applications such as CMF and can be used for load bearing applications in conjunction with fracture fixation devices. The subject invention may be used in both adults and pediatrics.

BACKGROUND OF THE INVENTION

After trauma, lost or damaged bone tissue can naturally remodel and repair fractures and small noncritical size bone defects. But, large bone defects (critical size) created by severe trauma, or tissue resection due to cancer or infection cannot heal on their own without help from therapeutic aids or materials designed to encourage bone regeneration. A bone substitute acts as a filler or scaffold for new bone growth, and bone grafting is a surgical procedure that uses bone graft to repair and rebuild diseased or damaged bones. Approximately 500,000, and more than 2 million bone graft procedures are performed annually in the U.S. and worldwide respectively. Market research estimates the global bone graft and substitutes sector to have been worth $2.68 billion in 2019 and will grow 5.1 percent annually through 2027.

The global craniomaxillofacial devices market size was valued at USD 2.45 billion in 2018 and is expected to witness CAGR of 6.0% during the forecast period. Products used in this market consist primarily of metallic plates and screw systems, but there is a rapid adoption of absorbable materials in applications where polymeric materials have adequate strength of materials for the repair requirements. It is also desirable to have materials that absorb to avoid the need for reoperation to remove a permanent plate. There is an unmet need to replace surgical plates and screws in the non load-bearing portions of craniomaxiofacial and small joint surgery. Surgical patient issues include time-consuming processes like placing plates and screws, high cost, patient discomfort, and a need for a second operation for metal implant removal. By contrast, the product of the present invention can solve these problems by fixing/adhering the bones with melt resorbable biocompatible polymer using a less invasive, less expensive, and much quicker approach, without the need for the second surgery. The molten materials can be placed around and at the interface of a bone graft or flap and the native bone tissue to fix the flap in place. The material will be heat flowable, absorbable, biodegradable materials with no drilling or screw type hardware for bone flap fixation of craniotomy.

Bone reconstruction and repair is often necessitated for the treatment of critically-sized bone defects (or other bone defects as described herein) or in some cosmetic surgeries (1). Such defects are referred to as bone loss of 2.5 $cm^2$ or greater that can be caused by trauma, tumors, congenital anomalies, infection, and skeletal diseases (1). The presence of these defects can lead to loss of independence, disability, or even mortality when not properly treated (2). In cosmetic surgeries, creating a scaffold that guides bone regeneration and the shape of newly developed tissue in a predictable fashion is essential (3). In such clinical applications, structural integrity is critical for successful tissue regeneration processes. Each year at least a million patients in the US have to undergo some type of clinical intervention to induce bone regeneration, resulting in a significant social and economic burden.

Bone usually maintains a robust ability to grow and self-regenerate (4). Critically-sized defects, however, are characterized by substantial tissue loss and destruction, and incomplete tissue regeneration. For example, 5-10% of 6 million bone fractures fail to heal properly, limiting recovery of full function (5). Despite the high prevalence of bone defects, their clinical treatment has remained controversial (4-6). Typically, the size of the defect dictates proper treatment options. To date, autografts serve as the gold standard in minor bone grafting, however, it is an expensive procedure that requires secondary surgery that can result in injury, morbidity and additional risks associated with bleeding, infection, inflammation and chronic pain (7). Allografts are the most commonly used alternative to autografts, but they are associated with the risk of a severe immune response, disease transmission, and insufficiency of donors (8). A key challenge in the use of bone grafts is the fixation of the graft in a way that the tissue integration and survival will not be affected.

Also, preventing potential infections due to the implantation which can be caused by improper use of sutures and staples is an important step. The current bone grafts/bone void fillers in the market are provided to the end-users (surgeons) in the form of granules, pre-formed blocks or ready to use putty/paste which are indicated for filling the bone void without providing a capability for a precise forming and setting in situ. Moreover, these products do not provide the chance of addition of live cells to the bone grafts during surgery.

The continuous need for the use of immunosuppressive drugs can lead to various life-threatening complications. Another solution is the use of bone cements, which are typically more suitable for non-load bearing bone defects of smaller sizes (9). Nonetheless, they usually suppress tissue regeneration and can lead to osteomyelitis. Therefore, there is an unmet need for the development of a robust treatment that can be used for the reconstruction of various bone defects with complex tissue architecture.

Regenerative strategies based on bioactive cues (i.e., growth factors) and cells (i.e., stem cell delivery) have drawn significant attention to facilitate bone healing and tissue regeneration. Despite this, the majority of these approaches have been limited by low cell engraftment and biological factors bioavailability (10, 11). Scaffold-based solutions that can be combined with biological materials and factors are more promising in creating structures that can mimic the structural, chemical, and physical characteristics of different bones (12, 13).

In the past decade, 3D printing and bioprinting has emerged as a potential technology that can create highly organized tissue constructs with the ability to mimic the complex architecture of various organs (14). 3D printed scaffolds for bone tissue engineering have typically been ceramic-, polymer-, and hydrogel-based (13). Despite the impressive level of structural details achievable with 3D printers, the implantation of the printed constructs has remained a major rate-limiting step (15, 16). Another important limitation of conventional 3D printing strategies is their time-consuming process for responding to urgent clinical needs. For example, in the case of a traumatic injury, it takes several hours to take 3D images from the injury site and reconstruct the files required for 3D printing. The printing process on its own can take up to several hours using traditional 3D printers. This could mean that a secondary surgery is needed for implanting the printed scaffold (17).

Improved compositions and techniques for the treatment of bone defects are needed.

SUMMARY

Provided herein is a strategy that allows a quick response for the treatment of bone defects or creating scaffolds to induce bone regeneration, e.g. in cosmetic applications. The strategy is based on the in situ printing of composite scaffolds which are antibacterial and/or osteoconductive.

An aspect of the invention provides a method of treating a bone defect or injury or reconstructing a new bone for cosmetic or non-cosmetic purposes in a subject in need thereof, comprising using a handheld 3D printer to apply a composite filament to the bone defect of the subject. In some embodiments, the composite filament comprises polycaprolactone (PCL) doped with zinc oxide nanoparticles and hydroxyapatite microparticles. In some embodiments, the method further comprises monitoring the application of the composite filament using a camera attached to the handheld 3D printer. In some embodiments, the bone defect has a diameter greater than 5 mm. In some embodiments, the bone defect has a depth greater than 5 mm.

Another aspect of the disclosure provides a filament or printing material for 3D printing. A heated, biodegradable flowable polymer provides adhesive properties which has the ability to adhere bone fractures or bone grafts together and can also be used as a replacement for conventional fracture fixation devices in non-load bearing indications such as CMF. In some embodiments, the filament or printing material can be used to replace the plate and screws in a craniotomy surgery and to attach the bone flaps to the bone without a need for drilling or using titanium screws and plates. The filaments or printing materials may comprise a low melting point polymer, e.g. a polymer having a melting point of 70° C. or lower, e.g. 60° C. or lower, e.g. between 40-70° C.

Another aspect of the invention provides a filament or printing material for 3D printing as a graft cage for retaining bone grafts and/or bone graft substitute in its desired location during healing for the treatment of critical-sized segmental defects in long bones (e.g., greater than 5 mm). A heated, biodegradable flowable polymer enables the surgeon to print a 3D graft cage/scaffold in situ in order to retain and stabilize the bone grafts or bone graft substitute, which allows faster nutrient access and bone restoration. The printed graft cage can be used with common rigid fixation devices such as intramedullary nails, plates/screws, and/or external fixation devices. Thus, at the site of the defect, a printed cage is formed in situ with bone graft therein or added thereafter, and the printed cage may be maintained in place with or without common rigid fixation devices.

In other aspects of the invention, the invention provides a filament or printing materials for 3D printing on any bone defect (e.g., bone defects having a nominal diameter greater than 0.2 mm and has a depth of greater that 0.2 mm).

In some embodiments, the filament or printing material comprises polycaprolactone (PCL) doped with zinc oxide nanoparticles and/or hydroxyapatite microparticles. In some embodiments, the PCL is present in a concentration of 25-85% w/w, e.g. 54-74% w/w. In some embodiments, the zinc oxide nanoparticles are present in a concentration of 0.5-1.5% w/w. In some embodiments, the hydroxyapatite microparticles are present in a concentration of 25-45% w/w. In some embodiments, the hydroxyapatite microparticles have a particle size of 1-5 μm. In some embodiments, the filament has a diameter of 0.5-5 mm, e.g. 1.5-2.5 mm. In some embodiments, the filament has a compression modulus of at least 200 MPa. Other low melting point, biocompatible and biodegradable polymers may be used in place of or in combination with PCL as the printing filament (e.g., alternative polyesters and/or polyurethanes similar to PCL, but also other polymer materials).

Another aspect of the invention provides a scaffold comprising a composite filament as described herein and cells deposited on the filament. In some embodiments, the cells are mesenchymal stem cells. Thus, the printed material produced (e.g., cage, scaffold, etc.) with the filament can include, for example, mesenchymal stem cells therein and/or on its surface.

Another aspect of the invention provides a method for performing a craniotomy which is the surgical removal of part of the bone from the skull, in order to enable access to the brain. In this aspect, the opening is closed and healed by printing in situ using the filament and methods described herein.

Another aspect of the disclosure provides a method for performing a pediatric orthopedic surgery employing printing in situ using the filament and methods described herein.

Another aspect of the disclosure provides a method for performing a craniomaxillofacial (CMF) surgery employing printing in situ using the filament and methods described herein.

BRIEF DESCRIPTION OF THE DRAWINGS

FIGS. 4A-F. Fabrication of composite filaments and their in situ printing using a handheld device. (A) Schematic of the extrusion-based device used for formation of filaments from the engineered composites to be used for printing. (B) SEM images of the cross-section of a typical filament at different magnifications showing the distribution of the HAp microparticles and ZnO nanoparticles within the filament. (C) A representative image of the handheld melt spun 3D printer used for printing of the filaments and the miniaturized integrated camera for on the fly monitoring of the printing quality. (D) Ex vivo printing of scaffolding materials into a defect formed within a fresh porcine jaw bone. The scaffolds stuck to the bone and did not detach. (E) Representative images showing the quality of the printing using different compositions. The formed imperfections create pores that are expected to support cellular infiltration. (F) A representative infrared (IR) image of the in situ printing process of scaffolding materials into a porcine jaw bone showing the distribution of temperature. The bone temperature did not exceed 40° C.

FIGS. 5A-D. In vitro bioactivity evaluation of printed scaffolds. (A-B) Antimicrobial activity of the printed scaffolds. (A) Representative SEM images from the surface of the printed scaffolds, showing the influence of ZnO nanoparticle incorporation on the growth of MRSA bacterium. (B) Colony forming unit (CFU) test representing the effect of ZnO nanoparticle incorporation into printed scaffolds after 15 h against gram positive MRSA. The results revealed the significant inhibitory effect of 1% ZnO nanoparticles on the growth of MRSA bacterium on the surface of the printed scaffolds. (n=3). (C-D) Viability assessment of cultured human Mesenchymal Stem Cells (hMSCs) on printed samples. (C) Viability assay for measurement of cell proliferation rate on the printed scaffolds over 7 days of culture (n=5). (D) Live/Dead viability assay of seeded cells 1 day post-incubation. The dashed lines represent the borders of the printed scaffolds. Data are represented as mean±SD ($p<0.05$ (*), $p<0.01$(**), ns 803 (not significant).

DETAILED DESCRIPTION

Embodiments of the invention provide compositions and methods for treating bone defects. In particular, a handheld melt spun 3D printer is used for depositing scaffolding material directly into a patient's body with the desired architecture without the need for expensive imaging and computational tools, or more significantly, surgical delay. In situ printing enhances the adhesion of the material to the surrounding tissue, which eliminates the risk of scaffold slippage improving the clinical outcome. Further embodiments provide a method of fixing, adhering, or gluing a bone fracture, a bone flap, a bone graft and/or pieces of bone in a subject in need thereof, comprising using a handheld 3D printer to directly deposit a filament or printing material inside, over and/or around the bone fracture, bone flap, or bone graft and/or at an interface of a flap and a bone within the subject.

Figure 8:
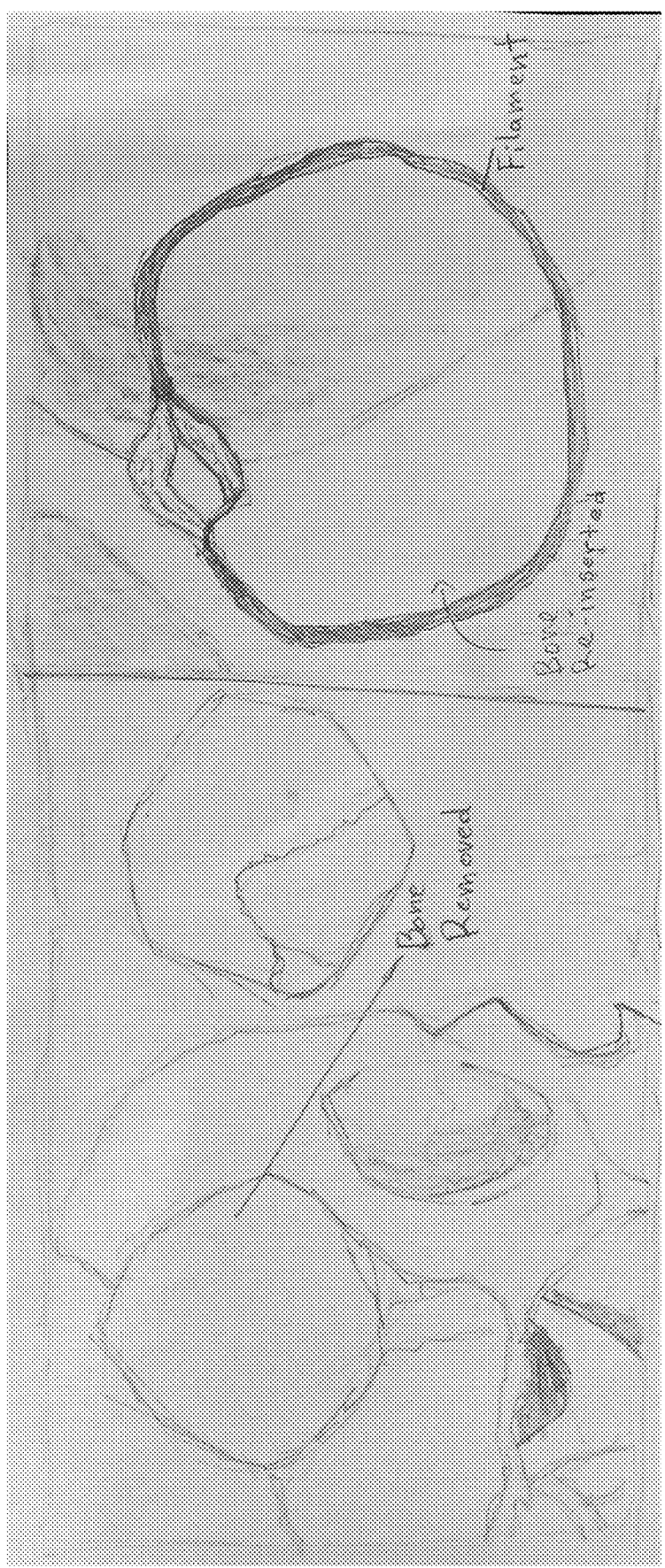
FIG. 8. Illustration of a craniotomy.

Some embodiments provide a method for performing a craniotomy which is the surgical removal of part of the bone from the skull, in order to enable access to the brain (FIG. 8). In the USA, over 225,000 craniotomy procedures are performed each year. The portion removed, referred to as the bone flap, is reattached after the need for brain access is concluded. The reattachment of the flap requires fixation, which is currently conducted by means of metallic/polymer plates and screws. Craniotomies are often a critical operation conducted by neurosurgeons. The reasons for the operations are varied, but it is often performed in patients suffering from brain lesions or Traumatic Brain Injury (TBI). In addition, it is performed to surgically implant devices for the treatment of disease states such as Parkinson's disease, epilepsy, and cerebellar tremor. The procedure is also widely used in neuroscience for extracellular recording, brain imaging, and for neurological manipulations such as electrical stimulation and chemical titration. Craniotomy is distinguished from craniectomy wherein the skull flap is not replaced and fixated.

Further embodiments provide a method for performing a pediatric orthopedic surgery which often requires repair methods that account for the growth of the bones and accomodate the growth or otherwise require removal. Thus, it is desirable to have fixation means which are absorbable. Bone adhesives are ideal for pediatric surgery as by the time the resorbtion reduces the material strength properties significantly, bony healing will already be completed. There is no need for any type of fixation device to remain as it serves no purpose beyond the healing period.

Figure 9:
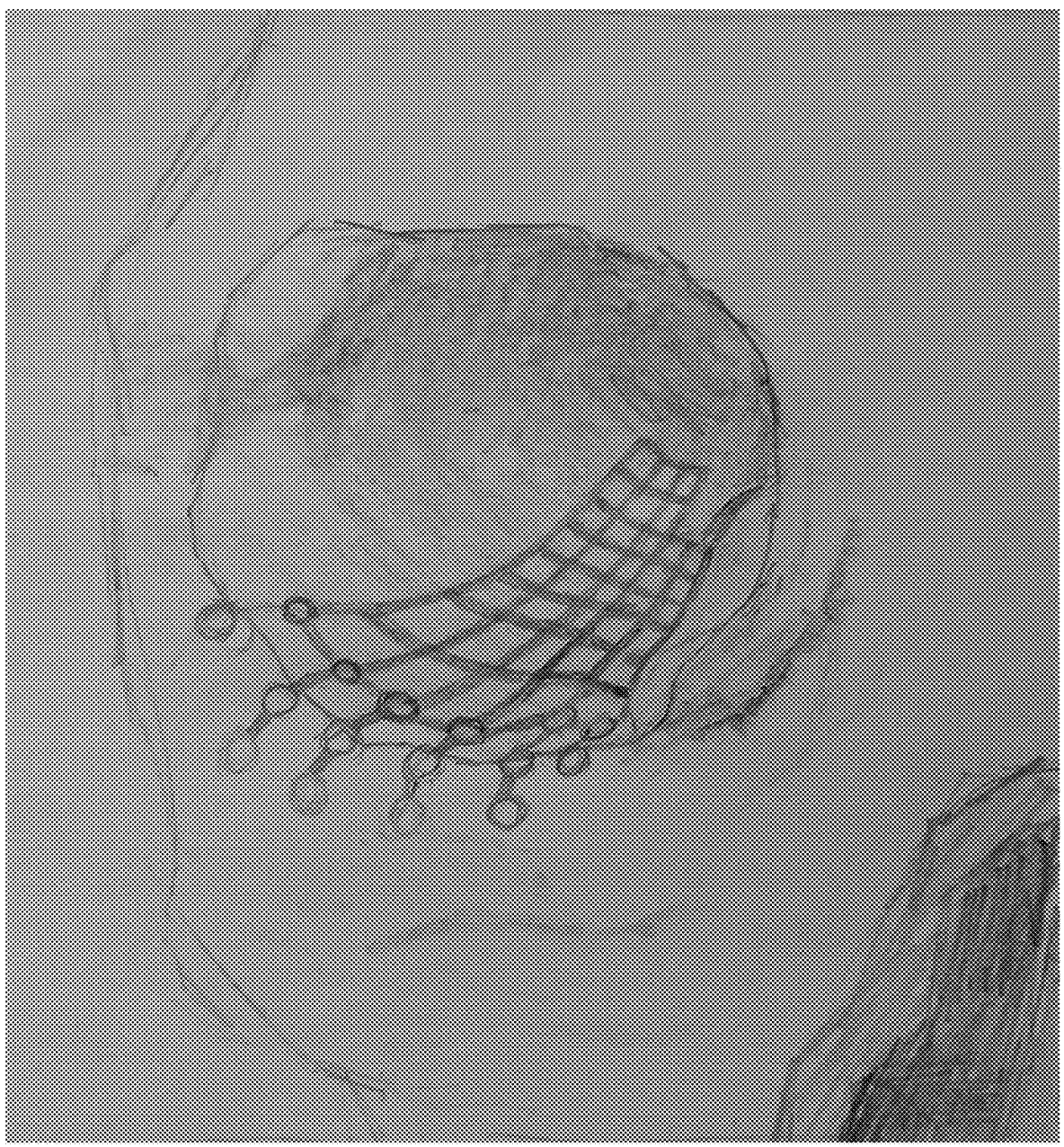
FIG. 9. Illustration of a craniomaxillofacial (CMF) surgery.

Further embodiments provide a method for performing a craniomaxillofacial (CMF) surgery which encompasses the treatment of pathological conditions of the face, jaws and skull, including trauma and the correction of facial skeletal deformity and dental deformity. An example is shown in FIG. 9. Since the 1980s, titanium plate fixation has been the preferred solution; however, titanium is not without its problems. Particular concerns center on the performance of titanium implants in the body and the effects on this, the restrictions to bone growth and implants migrating through the cranium in child patients. The present disclosure provides a CMF product system comprised of absorbable, biodegradable materials with no drilling or screw type hardware for trauma surgeries including all facial fractures and skull fractures. Types of CMF Surgery include CMF trauma, orthognathic surgery, craniofacial surgery, and mandibular reconstruction.

Unlike metal, polymer implants resorb over time, thus preserving the option of follow-on procedures and providing the body with superior soft tissue and bone revision. The repairs can be performed using adhesive only or adhesive in combination with a range of custom absorbable plates. The system described herein may be used in children and adults. The bone positioning system can be used to supplant all existing types of fixation.

Some embodiments of the invention provide composite filaments or other printing materials for 3D printing. The filaments or printing materials may comprise a low melting point polymer, e.g. a polymer having a melting point of 70° C. or lower, e.g. 60° C. or lower, e.g. between 40-70° C., e.g., polyurethanes, polyesters, etc. The filaments or printing material may comprise polycaprolactone (PCL) doped with zinc oxide particles, e.g. nanoparticles and hydroxyapatite particles, e.g. microparticles. In some embodiments, the filaments do not contain any other polymers, bioceramics, or antibiotic agents. It is preferred that the zinc oxide nanoparticles and hydroxyapatite microparticles are uniformly distributed throughout the fabricated composite filaments.

PCL, also referred to as (1,7)-polyoxepan-2-one or poly (hexano-6-lactone), is a biodegradable polyester with a low melting point of around 60° C. PCL may be prepared by ring opening polymerization of $\epsilon$-caprolactone using a catalyst such as stannous octoate. PCL is degraded by hydrolysis of its ester linkages in physiological conditions (such as in the human body) and is therefore useful as an implantable biomaterial. PCL is useful as the base polymer due to its biocompatibility, slow degradation, desired mechanical features, and low melting temperature. PCL may have a molecular weight ranging from 80,000 to 530 daltons, e.g., selected from 80000, 40000, 10000, 1250, and 530 daltons. In some embodiments, the PCL is present in the filament at a concentration of 1-100% w/w, e.g. 25-85% w/w, e.g. 54-74% w/w, e.g. 59-69% w/w. In some applications, other polymers, such as other polyurethanes or polyesters, may be used in combination with PCL or in place of PCL. The PCL or other polymer filament preferably includes zinc oxide nanoparticles and hydroxyapatite nanoparticles, as discussed below, but may also include other metals, metal oxides, ceramics, and minerals.

Zinc oxide nanoparticles are particles of zinc oxide (ZnO) that have diameters less than 100 nanometers. They have a large surface area relative to their size and high catalytic activity. ZnO nanoparticles may be synthesized by methods known in the art, e.g. by laser ablation, hydrothermal methods, electrochemical depositions, sol-gel method, chemical vapor deposition, thermal decomposition, combustion methods, ultrasound, microwave-assisted combustion method, two-step mechanochemical-thermal synthesis, anodization, co-precipitation, electrophoretic deposition, and precipitation processes using solution concentration, pH, and washing medium. In some embodiments, ZnO nanoparticles are synthesized by mixing $Zn(NO_3)_2 \cdot 6H_2O$ and $C_6H_{12}N_4$ at a 3:20 molar ratio in a microwave synthesis setup. As demonstrated in the Example, ZnO has antibacterial activity, is cytocompatible, and can improve osteogenesis. In particular, the incorporated ZnO particle inhibited the growth of bacteria on the surface of scaffolds which is important for the treatment of traumatic injuries. In some embodiments, the zinc oxide nanoparticles are present in the filament at a concentration of 0.1-20% w/w, e.g. 0.5-1.5% w/w.

Hydroxyapatite, $Ca_5(PO_4)_3(OH)$, is a naturally occurring mineral form of calcium apatite. Hydroxyapatite is the hydroxyl endmember of the complex apatite group and may be synthesized via several methods, such as wet chemical deposition, biomimetic deposition, sol-gel route (wet-chemical precipitation) or electrodeposition. As shown in the Example, the addition of hydroxyapatite reduced the hydrophobicity of the composition and improved the protein absorption. Hydroxyapatite has also been proven to possess osteoconductive properties and is biocompatible without showing toxicity in vitro or in vivo. In some embodiments, the hydroxyapatite microparticles have a particle size of 1-5 μm. In some embodiments, the hydroxyapatite microparticles are present in the filament at a concentration of, for example, 15-60% w/w; 25-45% w/w, 30-40% w/w, etc.

In some embodiments, the filaments may comprise any polymer and/or protein. For example, the filament may comprise one or more of functionalized or non-functionalized (e.g., derivatives including alkyl (C1-6), halogens, sulfonyl, hydroxyl, cyano, and other functional groups) polycaprolactone (PCL), polylactic acid, polyglycolic acid, poly(L-lactide-co-$\epsilon$-caprolactone), poly(ethylene adipate), poly(ethylene oxide), polyethylene co methacrylic acids, poly(tetramethylene oxide), PTMO, collagen, and gelatin, etc. and their mixtures. The polymers, proteins or their mixtures can be functionalized with different chemicals and chemistries. The polymers or their mixtures or proteins and their mixtures can be mixed with nanoparticles of any shape or microparticles of any shape or chemicals made from any material composition. Examples include, but are not limited to, a metal (silver, gold, magnesium, zinc, selenium, etc.), metal oxide, bioglass, small molecule drug, radiopaque agent, antibacterial compound, antibiotic, bioceramic, ceramic, oxygen generating material, crosslinking agent, vitamin, lipid, phospholipid, fatty acid, salt, biological factor, polysaccharide, nucleic acid, growth factor, hydroxyapatite, calcium phosphate, carbon nanotube, quaternary ammonium compound, graphene, graphene oxide, carbon derived material, liquid crystal, peptide, chitosan, alginate, silver nitride, platelet rich plasma, a blood derived material, hydrogen peroxide, and their combinations, etc. The concentrations of the nanoparticles or microparticles or chemicals can have any range, e.g. 1-99% w/w, e.g. 10-80% w/w, e.g. 25-45% w/w.

The filaments described herein may have a diameter of 0.1-15 mm, e g 0.5-15 mm, e.g. 1.5-2.5 mm. In some embodiments, the filament has a compression modulus of at least 1 kPa, e.g. at least 1 MPa, e.g. at least 200 MPa. The compression modulus of an elastic material is defined as the ratio of the applied stress to the resulting strain when that material is being compressed. This relationship can be represented by the following formula:

$$E = \sigma/\epsilon$$

Where:
E=Compression modulus
σ=Applied compressive stress
ε=Strain (compressed length/original length)

The filaments may be extruded using any portable, handheld 3D printer, e.g. a commercially available 3D printing pen (AIO Robotics, USA) that can melt and extrude polymers. In some embodiments, a camera is integrated with the 3D printer to allow "on-the-fly" inspection of the printing quality and adjustment of the speed to avoid printing defects. The process can be viewed on a monitor within, for example, an operating room, or images may be transmitted or displayed remotely/wirelessly on a computer, tablet, phone, or other device. The in situ printing of the filaments results in reasonable adhesion of the scaffolds to the surrounding tissues without increasing their local temperature to >40° C.

Handheld 3D printers can be easily operated using simple tactile controls to extrude filaments at a consistent rate and temperature. This flow rate can be customized as desired for fabricating differing scaffolds. The polymeric filaments may be first loaded into an opening at the posterior of the pen printer, where the filament is then extruded using electrical actuators controlled by a micro gearmotor. The printing temperature can be optimized and/or selectively controlled to allow printing of the filaments directly on bone/tissue without causing harm or discomfort.

In some embodiments, the handheld 3D printer comprises a housing defining a proximal end and a distal end opposite the proximal end, the housing including a receptacle for receiving a portion of a syringe or a filament assembly within the housing; a power supply disposed within the housing; an electric actuator disposed within the housing at a position sufficient to facilitate an operable coupling of the electric actuator to at least a portion of a plunger of the syringe assembly or a filament upon an insertion into the receptacle; a control interface positioned at least partially within the housing and including at least one control device operable from an exterior of the housing; a controller disposed within the housing and coupled to the power supply, the electric actuator, and the control interface; a heater that heats up at least part of the syringe or the filament upon an insertion into the receptacle, the controller configured to regulate a flow of power from the power supply to the electric actuator and heater based on signals received from the at least one control device to facilitate regulating an actuation of the plunger by the electric actuator; and a heated nozzle with a size or geometry that allows extrusion of materials out of the printer.

A camera may be located at the end or near the middle of the housing or close to the tip. The camera may have a mounting for adjusting its distance from the device.

Embodiments of the invention provide a scaffold as described herein comprising a composite filament and cells deposited on the filament. As shown in the Example, the printed scaffolds support the growth and proliferation, as well as the osteodifferentiation of cells such as human mesenchymal stem cells or preosteoblasts.

Figure 10:
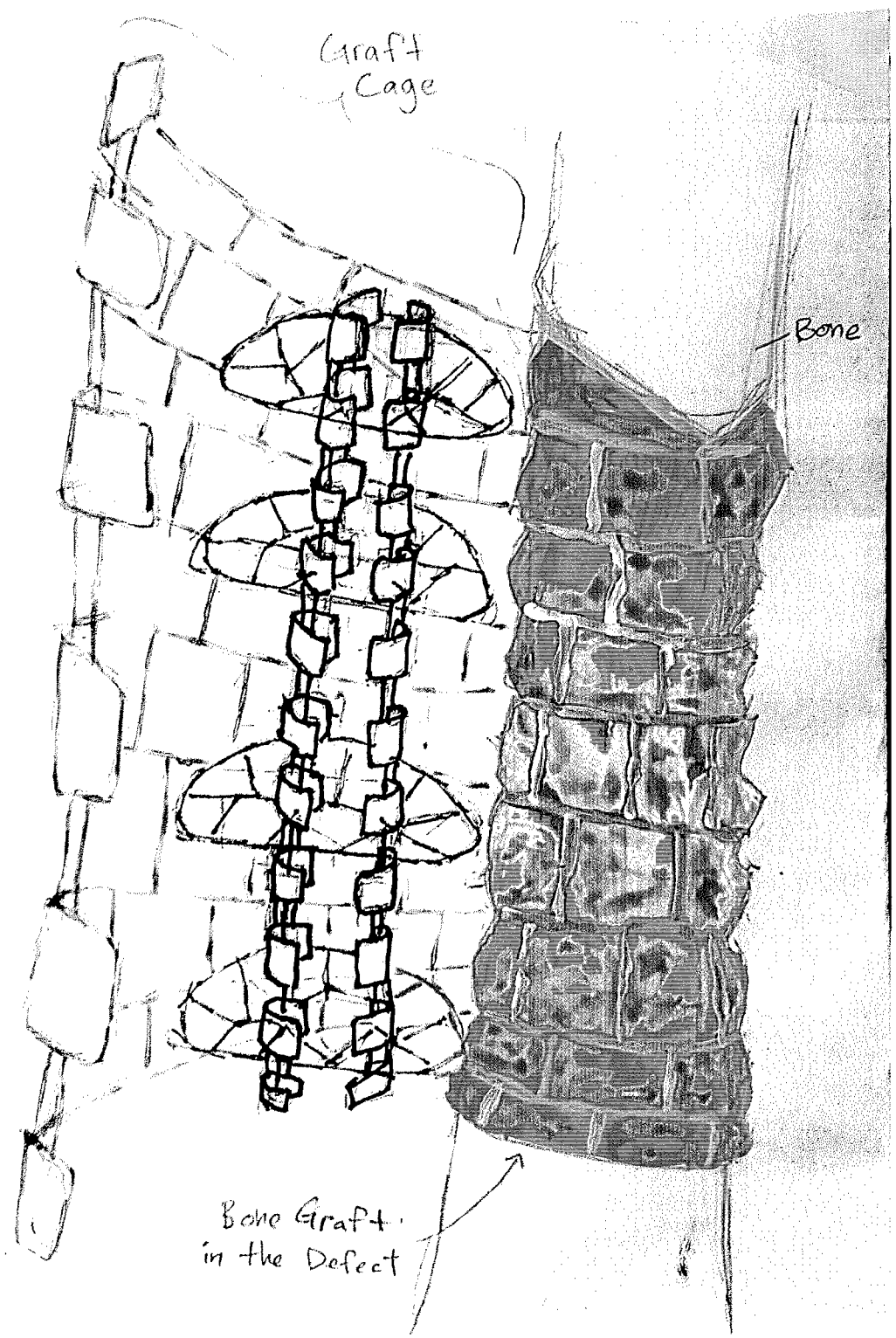
FIG. 10. Illustration of a bone graft or bone graft substitute held in place at a critically sized bone defect using a cage formed by printing with the filament.

The filaments described herein are used to treat (i.e. fill in) bone and tissue defects/cavities. A bone defect is a lack of bone where it should normally occur. Bone defects may be caused by trauma, tumor, or infection (e.g. osteomyelitis). In some embodiments, the bone defect has a diameter greater than 2-5 mm (e.g. 2-20 mm). In some embodiments, the bone defect has a depth greater than 2-5 mm (e.g. 2-20 mm). The bone defect may have an irregular shape and involve multiples tissues. The compositions and methods described herein may be used on any bone type, e.g. for facial fractures affecting the nasal area, zygoma-maxillary complex, orbital area or mandible. The printed filaments/scaffolds are used to induce bone regeneration within a bone defect. The printer can be used in an emergency room to minimize the response time between the injury and treatment. It also can be used by non-professionals remotely guided by clinician. A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals. In addition, as shown in FIG. 10, the filament or composition can be used to print a cage that is used to retain a bone graft or bone graft substitute in place in a bone defect (e.g., a critically sized defect in long bones) during the healing process. The cage can be applied and be used during the healing process with or without the assistance of traditional fixation devices (e.g., screws, plates, etc.).

In some embodiments, a method as described herein is performed as part of a neurosurgical craniotomy, a craniomaxillofacial (CMF) surgery reconstruction, a hand or other extremity surgery, an adult or pediatric orthopedic surgery, treatment of a facial fracture, or a spinal surgery.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Bone defects are commonly caused by traumatic injuries and tumor removal and critically sized defects overwhelm the regenerative capacity of the native tissue. Reparative strategies such as auto, xeno, and allografts have proven to be insufficient to cure these defects. For the first time, we introduce the use of handheld melt spun three dimensional printers that can deposit scaffolding materials directly within the defect site to properly fill the cavity. Engineered composite filaments were generated from poly(caprolactone) doped with zinc oxide nanoparticles and hydroxyapatite microparticles. The use of PCL-based materials allowed low-temperature printing to avoid overheating of the surrounding tissues. The in situ printed scaffolds showed moderate adhesion to the bone tissue, which can prevent scaffold dislocation. The printed scaffolds showed to be osteoconductive and supported the osteodifferentiation of mesenchymal stem cells. Biocompatibility of the scaffolds upon in situ printing subcutaneously in mice showed positive results.

Materials and Methods

Materials

PCL (Mw=80,000 Dalton), HAp (2.5 μm of particle size), zinc nitrate dehydrate ($Zn(NO_3)_2 \cdot 6H_2O$; 99.99%), hexamethylenetetramine ($C_6H_{12}N_4$; 99.99%), PBS, sodium dodecyl sulfate (SDS) and chloroform were purchased from Sigma-Aldrich (MO, USA). DPBS and FBS were purchased from Thermo-Fisher Scientific (USA). ZnO nanoparticles were synthesized by mixing $Zn(NO_3)_2 \cdot 6H_2O$ and $C_6H_{12}N_4$ at a 3:20 molar ratio in a microwave synthesis setup (Milestone, Italy). Details of the ZnO synthesis can be found elsewhere (23).

Materials Characterization

The presence of PCL, HAp, and ZnO in the composite filament was confirmed by FTIR spectra using an ATR-FTIR spectrometer (Thermo Fisher Scientific, USA). The filament was placed on a Smart SpeculATR™ accessory with germanium substrate, and the spectra were collected across the 4000-400 $cm^{-1}$ wavenumber range.

Crystalline structures of the composite filament and its individual components were analyzed according to XRD using an ULTIMA IV XRD system (Rigaku, Japan) attached with Cu Kα radiation. PCL and the composite filaments were loaded as a thin film (200 μm thickness), whereas ZnO and HAp were loaded in their original powder form.

Cross-sections of the prepared filaments were visualized using SEM (FESEM, JEOL JSM 7600F, Tokyo, Japan). An Auto Fine Coater (JFC-1600, JEOL JSM 7600F, Tokyo, Japan) was used to sputter coat the samples with platinum for 30 seconds at 30 mA and about 3.5 Pa. Elemental mapping of the cross section was achieved using EDX.

For the biodegradation study, the filaments were dipped into a 1×PBS solution and were kept at 37° C. over a period of 16 weeks. At each time point (a two week interval), the dry weight of the samples was measured and the values were used for the weight loss calculation.

To assess protein absorption, filaments were rinsed with DPBS and then were immersed in a 10% (w/v) FBS solution for 24 h. The samples were washed again by DPBS and dipped into a 2% (w/v) SDS solution for 3 h. The concentration of proteins in SDS was determined using the Nanodrop® 2000 system (Thermo Fisher Scientific). The amounts of proteins were calculated according to UV absorbance at a wavelength of 280 nm. Bovine serum albumin (BSA) was used as a correction factor.

WCA measurements for the composite were performed at room temperature and 40% humidity using a drop shape analyzer (DSA 100, Kruss, Germany) 5 μL of deionized water was carefully placed on the surface of the flattened composites, and shape of the droplet captured immediately after the water touches on the sample surface. The angle between the drop contour and the surface baseline was determined as the WCA.

DSC test (DSC-60, Shimadzu Corporation, Japan) was used to analyze the thermal transition behavior of the composites. The samples were loaded in a low-volume aluminum crucible (S08/HBB3740), and the sample temperature raised up from 25° C. to 150° C. at 5° C./min, then dropped down to 25° C. with 5° C./min cooling rate. Nitrogen gas with 35 mL/min was swept over the cell as a purging gas.

Mechanical Characterization

Mechanical durability of the composite filament was evaluated using compression testing mode using a Discovery Hybrid Rheometer (DHR-3, TA instrument, USA). A piece of cylindrical filament (height/diameter=2:1) was compressed at 10 μm/s of head speed until 50% strain.

Rheological behavior of the composite filaments was determined using a Discovery Hybrid Rheometer (DHR-3, TA instrument, USA) with a 40 mm diameter parallel-plate geometry. The storage modulus (G') and loss modulus (G") of the filaments as a function of temperature were determined using a temperature ramp oscillation measurement. The composites were first molten at 150° C., then cooled down to 65° C. at 5° C./min A 2% strain and 10 rad/s of angular frequency was applied during the measurement.

Mechanical adhesion strength was analyzed through normal adhesion tests between the printed composite filament and porcine jaw bone. Rectangular samples (10×10×40 mm) were prepared with a freshly cut porcine jaw bone and printed composite filament. Next, they were cooled to 20° C. before testing. Measurements were assessed using an Electroforce® 3220 (TA instruments) mechanical tester. Specimens were stretched at a displacement rate of 0.167 mm/s until complete failure or separation at the interface of composite filament and bone occurred.

Filament Preparation

The composite pellets were prepared by solvent casting method using chloroform (100 mL for 15 g of composite) primary to extrusion. First, HAp and ZnO were added into chloroform, then PCL pellets were slowly added into the mixture under vigorous stirring. Afterward, the mixture was tightly covered and gently stirred overnight at 80° C. Subsequently, the mixture was poured into a large area steel pan and dried in an oven at 100° C. for 2 h.

A custom-made desktop filament extruder with 1.75 mm of the nozzle was used to prepare the composite filament. The solvent casted composites were cut into small pieces before feeding into the extrusion. The die temperature was 75° C., and the rotation speed of the screw was 30 rpm. The extrusion was performed vertically, and a water bath (4° C.) was placed just under the extrudate to collect the produced filament.

Printability Analysis

A commercially available 3D printing pen (AIO Robotics, USA) was used for the printability assessment of the fabricated composite filaments. Porcine jaw bone was cut using a Dremel saw/drill. Cavities of irregular geometry ranging from 2-5 mm in diameter were drilled into the jaw bone. The thermal activity of the filament printed into the cavities was monitored with a handheld thermal imaging camera (FLIR®, USA).

Antibacterial Studies

Colony Counting 3D printed filaments were cut into small identical pieces (3 mm×3 mm) in triplicate. Each sample was placed in a single well of a 48 well plate followed by UV sterilization for 30 min before starting any experiment. To demonstrate the antimicrobial properties of the 3D printed filaments MRSA was used as bacterial model. A single colony of MRSA bacterium was mixed in 5 mL of TSB (22092 Sigma-Aldrich, USA), and then placed in a shaker incubator overnight (at 37° C., 200 rpm). After 24 h incubation, the optical density (OD) of the bacterial suspension was set on 0.52 @ 562 nm absorbance, which is in accordance to a density of 109 CFU/ml. Then, the resulting suspension was serially diluted until a density of 106 CFU/ml was obtained. Subsequently, 500 µl of the 106 CFU/ml suspension was directly added on top of each well, and the plate was incubated overnight at 37° C. and 5% $CO_2$. After 24 h incubation, the samples were carefully washed with PBS (×3) to remove any non-adherent bacteria. For the CFU assay, samples were placed in microcentrifuge tubes and 500 µl of PBS was added onto each tube. All tubes were then vigorously vortexed (3000 rpm, 15 min) to detach all bacteria from the samples and release them into the solution. Each bacterial suspension was serially diluted in PBS over 5 different logarithmic dilutions (100×; 1,000×; 10,000×; 100,000×; and 1,000,000×). Next, three drops (each 10 µL) of each dilution (1000× and above) were separately seeded on agar-TSB plates. The plates were then incubated (37° C. and 5% CO2) for 15 h. Eventually, the number of bacterial colonies was counted, and to calculate CFU values the dilution factor was employed.

Bacterial Adhesion

To demonstrate bacterial colonization along 3D printed filament surfaces, an SEM technique was performed. After overnight incubation of the samples with the bacterial solution of 106 CFU/ml, the samples were gently washed with PBS (×2). Then PBS was completely removed and replaced by 500 µl of 4% paraformaldehyde fixative solution. All filaments were kept in the fixing solution (4 days, at 4° C.) before serially dehydration in a graded series of ethanol (50%, 70%, 80%, 90%, and 100%). The dehydrated samples were dried using critical-point drying system equipped with carbon dioxide and finally sputter-coated with a 5 nm thin layer of platinum before being imaged via a Hitachi S-4800 SEM.

In Vitro Bioactivity of Scaffolds

Cell Seeding hMSCs (RosterBio MSC-003) were cultured on the printed samples. Samples were prepared by printing the filaments using the handheld printer similar to that shown in FIG. 4G, cut into the same dimension (10×10×3 mm in 2 layers) and subsequently sterilized under UV light for 10 mM, immersed in 70% ethanol, and washed with PBS. The hMSCs were expanded to prepare for seeding on the samples in their complete growth media made of minimum essential medium α (MEM-α) supplemented with 16% (v/v) FBS, 100 U/mL penicillin, 100 ng/mL streptomycin, 2 mM L-glutamine and incubated at 5% CO2 and 37° C. Cells were passaged every 3-4 days at ~80% confluence with trypsin-EDTA (0.1%), and their media was changed every other day. The hMSCs were subsequently harvested at passage 4 and cultured on sterilized samples by the concentration of 30,000 cells/cm$^2$ and maintained in the complete growth media for further experiments.

Cell Viability Assessment

The initial viability of cells after one day seeding on scaffolds was characterized using a Live/Dead™ Viability/Cytotoxicity Kit (Invitrogen) as specified by the manufacturer's instructions. Briefly, samples were incubated with a solution of calcein AM (green color, viable cells) and ethidium homodimer (red color, non-viable cells) probs in DPBS for 15 mM and then washed with DPBS. Samples were imaged using a Zeiss fluorescent microscope. The long-term viability and proliferation of cells were evaluated after 1, 3 and 7 days seeding by measuring their metabolic activity using PrestoBlue® Cell Viability Reagent (Invitrogen). At each time point, samples were incubated with a 1:9 ratio of reagent in growth media for 1 h at 37° C. and the fluorescence intensity of the solution was measured using a Cytation 5 Cell Imaging Multi-Mode Reader (Biotek, USA) at 540 nm (excitation)/600 nm (emission).

Cell Differentiation

After 3 days of culturing hMSCs on samples, their growth media was replaced with differentiation media composed of complete growth media supplemented with 10 mM β-glycerophosphate (Sigma), 10 nM dexamethasone (Sigma) and 50 µg/mL L-ascorbic acid (Sigma). Seeded samples were kept in differentiation media for up to 35 days for further experiments and their media changed every 3-4 days.

Immunostaining

After 21 and 28 days post differentiation, cell-seeded constructs were fixed with 4% (v/v) paraformaldehyde for 15 mM, then permeabilized by incubating with 0.3% (v/v) Triton X-100 in PBS for 10 mM Samples were washed 3 times with PBS and then were incubated with blocking solution (1% (w/v) BSA in PBS containing 22.5 mg/mL glycine and 0.1% Tween 20 for 1 h at room temperature. After washing samples with PBS for 3 times they were incubated in 1/200 dilution of the first antibodies (Abcam) against osteopontin (OPN, ab69498), bone sialoprotein (BSP, ab52128) (on fixed samples from day 28), RUNX2 (ab76956) and collagen I (ab34710) (on fixed samples from day 21) in 0.1% (w/v) BSA in PBS solution overnight at 4° C. Samples were washed and incubated with the secondary antibody goat anti-mouse IgG H&L (Alexa Fluor® 488) (ab150117) and goat anti-rabbit IgG H&L (Alexa Fluor® 594) (ab150080) and DAPI with the dilution factors of 1/500 and 1/1000, respectively, for 1 h at 37° C. Samples were washed and imaged using a confocal microscope (Zeiss LSM 800).

Assessment of Mineralization

The osteogenic activity of the osteodifferentiated hMSCs and their capability for mineral deposition were demonstrated using an alkaline phosphatase activity assay and xylenol staining.

Alkaline Phosphatase Activity Assay

ALP activity was determined by using the alkaline phosphatase assay kit (Colorimetric, Abcam, ab83369) on seeded samples at day 10 post differentiation according to the manufacturer's instructions. Briefly, 80 µL of the conditioned culture media of samples was added to 50 µL of a 5 mM p-nitrophenyl phosphate (pNPP) solution and incubated at room temperature for 1 h. The ALP present in the media used pNPP as a phosphatase substrate and changed its color after dephosphorylation. The absorption of the solution was measured at 405 nm using the same BioTek spectrophotometer.

Xylenol Staining

Calcium deposition from osteodifferentiated cells was assessed through xylenol orange staining 35 days after differentiation. Xylenol orange powder was dissolved in distilled water and sterile filtered to prepare a 20 mM stock solution (Sigma-Aldrich, St. Louis, Mo.). The cell culture media from the seeded scaffolds were replaced with a concentration of 20 µM of stock solution in cell culture media and incubated for 12 h at 5% $CO_2$ and 37° C. Culture media was refreshed after incubation time and imaged using the same confocal microscope at 570 nm (excitation)/610 nm (emission).

Animal Study

Nine week old C57BL/6 mice were purchased from the Jackson Laboratory (Charles River, Envigo (Harlan Labs) (Bar Harbor, Me.) weighting between 20 and 25 g and housed in the Life Science Annex animal facility at University of Nebraska for a one week acclimation period before the subcutaneous implantation injury procedure. Mice were divided into three study groups receiving in situ printed 1) P, 2) PZH1 and 3) PZH2 scaffolds. All animal operations were authorized by the Institutional Animal Care and Use Committee (IACUC) of the University of Nebraska, Lincoln.

On the day of surgery, an anesthesia system (VetFlo®, Kent Scientific, Torrington, Conn.) was used for anesthetizing all the animals by 2% isoflurane (USP-PPC) through a nose cone. The dorsal back hair of the animals was shaved and the skin was sterilized prior to creating incisions. To implant the scaffolds, two 8 mm incisions were made on the dorsal section of each mouse (left and right). Each composite scaffold was printed within each subcutaneous pocket of the mouse and the incisions were then sutured. All animals were carefully monitored for the following 7 and 28 days by animal care services. A total of n=6 animals per group per time point were used.

Histology

After 1 and 4 weeks, animals were sacrificed. Samples with surrounding tissue were biopsied, fixed by immersion in 10% neutral buffered formalin, processed on a Tissue-TEK VIP 5 tissue processor, and embedded in paraffin blocks for sectioning. Then, 4 µm slide sections were made and stained with H&E and Masson's trichrome. The H&E slides were stained on a Leica ST5020 stainer, and the Masson's trichrome slides were stained by hand. All histological evaluation was performed by a board certified veterinary anatomic pathologist that was blinded to the treatments.

Immunohistochemistry Staining

Tissue sections on slides were first deparaffinized by xylene then hydrated with graded ethanol series. A heat-induced antigen retrieval followed from each antibody protocol (citrate buffer 10 mM, pH: 6 for CD68 and Tris/EDTA Buffer 10 mM, pH: 9 for CD31) at 90° C. for 30 min. Then, each slide was washed with PBS-Tween 20 (0.05%) 3 times each for 5 mM, then blocked with 10% goat serum, 0.05 Tween 20 and 1% BSA in PBS for 1 h. The CD68 (ab125212) and CD31 (ab56299) primary antibodies were used at 1 µg/ml concentration and 1:200 dilution ratio, respectively, and incubated overnight at 4° C. A secondary antibody goat anti-mouse IgG H&L (Alexa Fluor® 488) (ab150117) was used at 2 µg/ml (shown in green) for 2 h to visualize the staining and image with Zeiss® fluorescent microscope.

Statistical Analysis

Results are presented in the form of mean and ±standard deviation of independent measurements. Statistical analyses were conducted in GraphPad Prism with 95% confidence intervals (a=5%). Statistical significance between treatments is denoted with an asterisk in the corresponding figures. ANOVA testing was conducted with Tukey's post hoc analysis.

Results

Figure 1A:
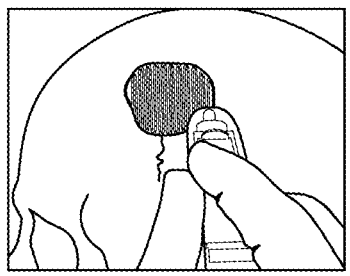
FIGS. 1A-C. Schematic demonstration of the concept of in situ printing of the composite. (A) Schematic view of the integrated camera on pen. (B) Schematic of the material composition. (C) The composite polymeric systems of PCL, Hydroxyapatite (Hap) microparticles, and ZnO nanoparticles is printed using a handheld printer with an integrated camera.
Figure 1B:
Figure 1C:
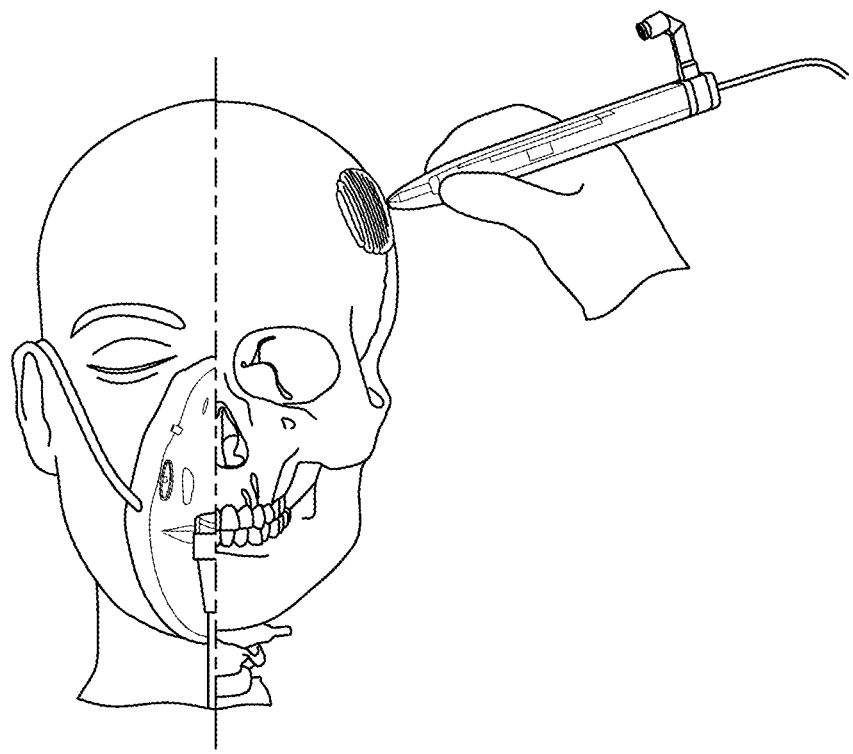

To facilitate the response to bone injuries and defects, composite PCL-based filaments containing HAp as an osteoconductive material and ZnO with both antibacterial and osteoinductive properties were fabricated (FIG. 1A-1C). The strategy for facilitating the injury response was to use handheld 3D printers for printing the fabricated filaments. This strategy enables responders and care providers to control the depositing system and create a 3D scaffold in situ. An integrated camera enables the online monitoring of the quality of the printed scaffolds by the care provider on-site or off-site via distant video surgery. PCL was selected as the base polymer due to its biocompatibility, slow degradation, desired mechanical features, and low melting temperature. Alternative polymers, such as substituted PCL, polyurethanes and polyesters may also be employed in the practice of the invention. PCL has also been successfully used in bone tissue engineering applications (19-21). HAp has also been proven to possess osteoconductive properties and has been used both in research and clinical efforts (20, 22). HAp is biocompatible and even at pure form has not shown toxicity in vitro and in vivo (22). To be able to form 3D printing filaments, we used 30% and 40% (w/w) of HAp. In the practice of the invention, alternative osteoconductive materials may be employed. ZnO is widely used as an antibacterial compound in various applications (23, 24). Recently, it has been shown that ZnO at moderate levels is cytocompatible and can improve osteogenesis (18, 24). Thus, 1% (w/w) of ZnO was added to the composition. However, alternative antibacterials may also be used in the practice of the invention.

The various composites fabricated and tested in this study can be found in Table 1.

TABLE 1

Various Composites of Interest

| No. | Sample designation | PCL | HA | ZnO |
|---|---|---|---|---|
| 1 | P | 100% | — | — |
| 2 | PZ | 99% | — | 1% |
| 3 | PZH1 | 69% | 30% | 1% |
| 4 | PZH2 | 59% | 40% | 1% |

Material Characterization

Figure 2A:
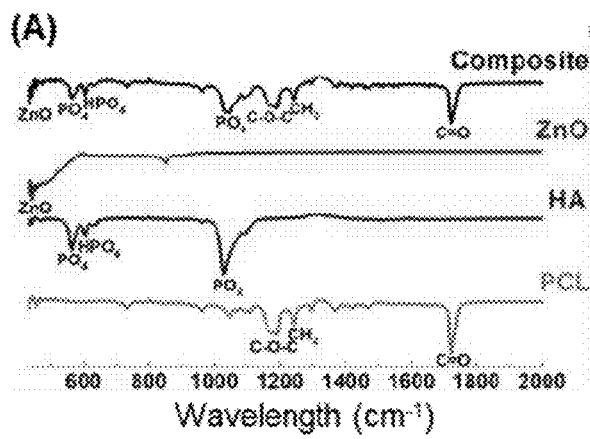
FIGS. 2A-F. Physicochemical characterization of the composite. (A) Fourier-transform infrared spectroscopy (FTIR) spectra and (B) X-ray powder diffraction (XRD) pattern of the composite and its individual components, which show that chemical and crystalline structure of the individual materials remained unchanged during the formation of the composite. (C) X-ray spectroscopy (EDX) spectra of the composite reveal its elemental composition. (D) Mass loss percentages of composite materials in PBS demonstrate a tunable biodegradation rate of the composition. (E) Protein adsorption capacity and (F) water contact angle of the PCL based composite filaments. Addition of HAp proportionally improved wettability and protein adsorption capacity of PCL.

The chemical structure of the composite filaments and the individual materials was examined by Fourier-transform infrared spectroscopy (FTIR), which showed that spectra of the composite filament were the combination of its individual components (FIG. 2A). The absorption bands at 1723 cm$^{-1}$ (C=O stretching), 1188 cm$^{-1}$ (C—O—C symmetric stretching), and 1242 cm$^{-1}$ (CH$_3$ symmetric stretching) in the composite filament were attributed to characteristics of PCL. On the other hand, a strong absorption band at around 1023 cm$^{-1}$ (P—O asymmetrical bending vibrations), and two less intensive absorption bands at around 564 cm$^{-1}$ and 605 cm$^{-1}$ (P—O—P deformation vibrations) corresponded to characteristics of HAp. Additionally, a peak appearing at around 430 cm$^{-1}$ revealed the presence of ZnO in the filament.

Figure 2B:
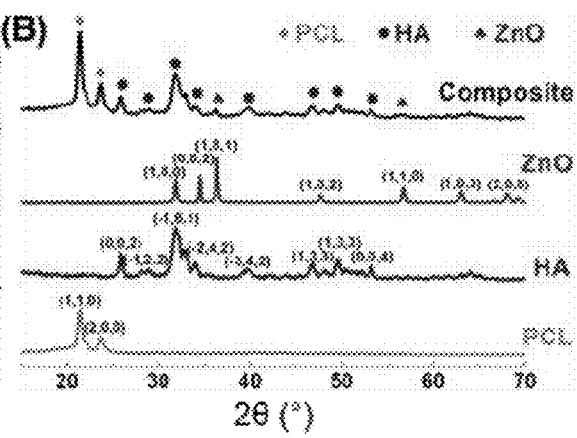
Figure 2C:
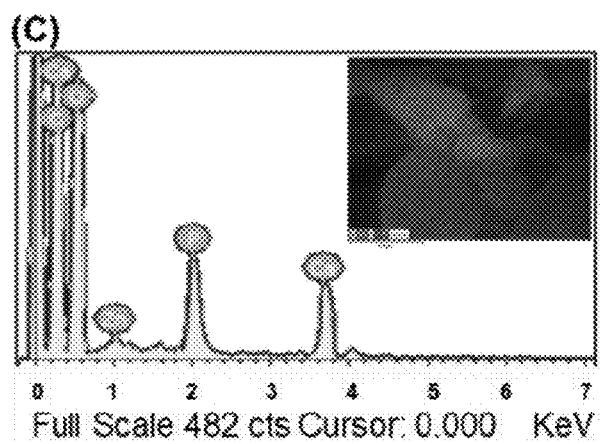

Similarly, the X-ray diffraction (XRD) pattern of the composite filaments confirmed that the crystalline structure of the individual materials, including ZnO, was not altered through the mixing, melting and extrusion process (FIG. 2B). The peaks at 21° and 23.5° in the composite were attributed to the XRD pattern of PCL, and the additional peaks observed in the range of 25~60° mainly corresponded to the diffraction of HAp. Although most of the XRD peaks for ZnO overlapped with HAp, a clear peak appeared at 36.3°, identical to the crystalline phase of ZnO. Elemental analysis by Energy Dispersive X-ray spectroscopy (EDX) revealed the presence of all major elements in the filaments, even a corresponding peak for zinc appeared, regardless of its low concentration (FIG. 2C).

Figure 2D:
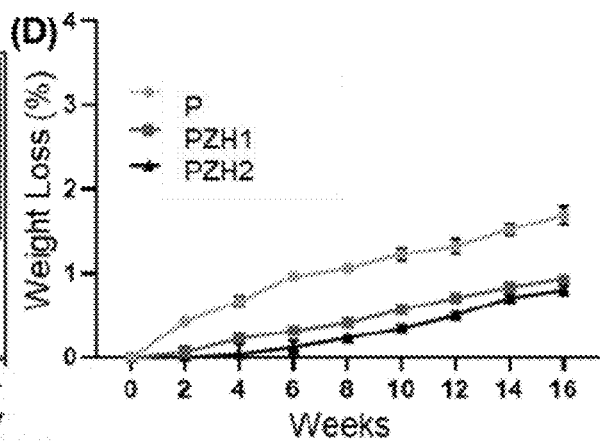
Figure 2E:
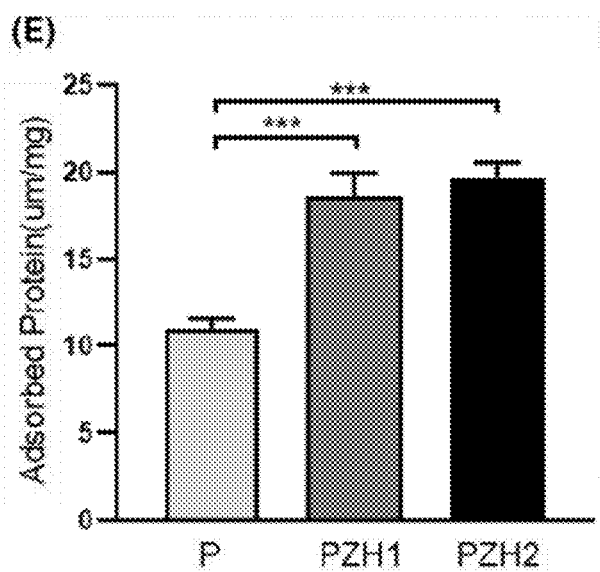
Figure 2F:
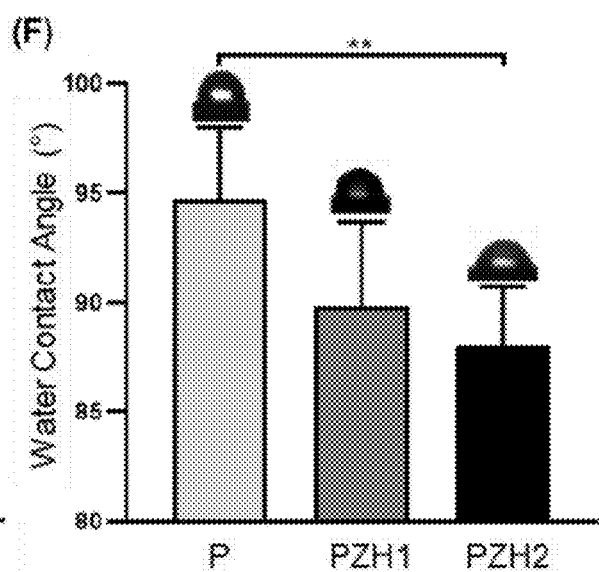

The degradation rate of the composition was assessed according to mass loss percentage over time after immersing them in a phosphate buffered saline (PBS) solution. Within three months, the pure PCL filament showed approximately 1.5% of mass loss, whereas the mass loss for PHZ1 and PHZ2 was approximately 0.9% and 0.7%, respectively (FIG. 2D). Protein adsorption capacity of the filaments was evaluated by immersing them in 10% (v/v) of fetal bovine serum (FBS) in Dulbecco's modification of Eagle medium (DMEM) for 48 h at 37° C. The results showed that the incorporation of HAp proportionally increased protein absorption which could improve cell attachment and biocompatibility of the printed composite scaffolds (FIG. 2E). Next, water contact angle (WCA) measurements were performed on the surface of the printed composite scaffold, which showed that the addition of HAp reduced the WCA of PCL-based composite (FIG. 2F). Specifically, the PZH2 composite scaffold had hydrophilic properties (WCA)<90°. Finally, since the melting and crystallization behavior of the filament scaffolds play an important role in fused deposition molding (FUM) based 3D printing, differential scanning calorimetry (DSC) analysis was conducted. The obtained data implied that the incorporation of HAp and ZnO slightly decreased the melting temperature and enhanced the crystallinity of PCL.

Mechanical Characterization of Composite Materials

Figure 3A:
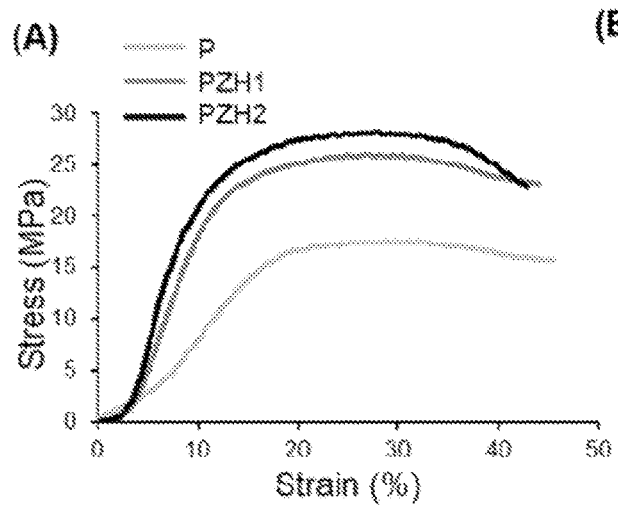
FIGS. 3A-D. Assessment of mechanical and adhesion properties of the engineered composites. (A) Representative stress-strain curves of the compression tests performed on circular disks made from the composites. (B) The compressive moduli of various compositions. The compositions containing HAp showed a significantly higher compressive modulus than pristine PCL, while there were no significant differences between $PZH_1$ and $PZH_2$ suggesting an insignificant effect of HAp concentration at the tested range; n=5. (C) The ultimate adhesion strength of the tested compositions to porcine jaw bone. The adhesion strength was slightly increased by the addition of HAp microparticles. (D) Representative images showing the test setup and a typical failure at the interface suggesting limited chemical interaction between the composites and bone tissue. ($p<0.05$ (*), $p<0.01$(), $p<0.001$(*), 774 $P<0.0001$(****), n=5).
Figure 3B:
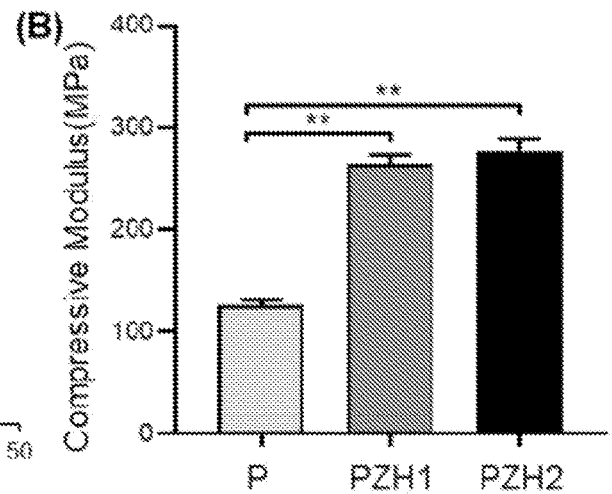

The mechanical strength of the composite materials was evaluated by compressing them up to 50% strain. The maximum tolerated stress was recorded at 20-30% strain (FIG. 3A). Further compression of the samples resulted in their breakage. Compared to pristine PCL (16.9±0.8 MPa), the composite filaments exhibited significantly higher compression strength, and the increase in strength was found to be proportional to the percentage of HAp in the composition (e.g.: 23.9±2.8 MPa for PZH1 and 28.4±1.1 MPa for PZH2). In addition, the compression modulus of the composites was compared and analyzed. Pristine PCL had a compression modulus of 126±4.6 MPa, while the modulus of the composite materials was almost twice as high as those of PCL (FIG. 3B). The results clearly showed a hardening effect of HAp particles within the PCL matrix, and mechanical sustainability of the composite scaffolds for bone tissue regeneration.

Rheological behaviors of molten PCL and composite materials (such as dynamic modulus and complex viscosity) were evaluated as a function of temperature. Both dynamic moduli (storage and loss modulus) and complex viscosity for composite scaffolds were higher than those of PCL in all the tested temperature ranges, especially near the melting temperature of PCL. At 65° C., the storage modulus of the composite scaffolds (180 kPa) was found to be two times higher than that of pristine PCL (90 kPa). While the differences became lower at higher temperatures, even a similar complex viscosity was observed for both samples above 140° C. This result implies that there was a strong hydrodynamic interaction between PCL and HAp/ZnO particles (25). This information is extremely important for the selection of compositions that are easy to be in situ printed. Since keeping the melting temperature as low as possible is important in avoiding the overheating of host tissues at the injury site, it is expected that in situ printing of composites with high concentrations of HAp/ZnO (e.g.: above 40% of HAp) would be extremely challenging.

Figure 3C:
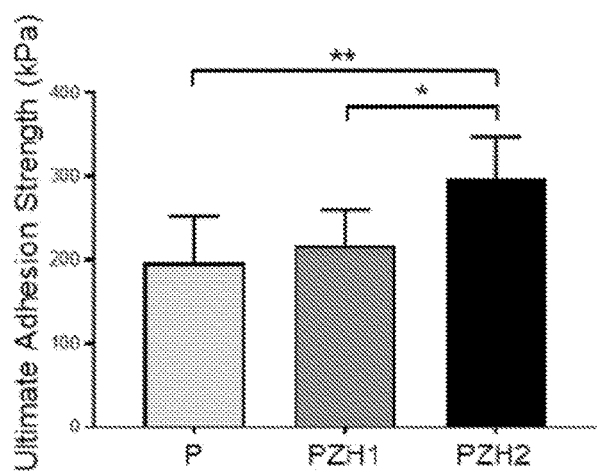
Figure 3D:
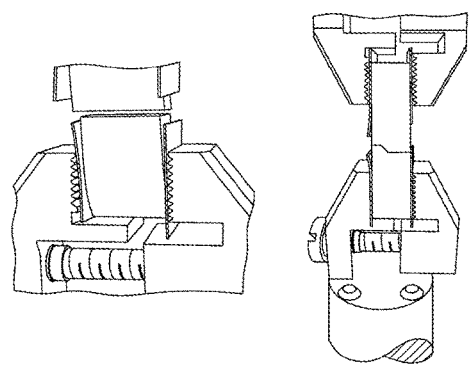

Ex vivo adhesion strength was analyzed through normal adhesion tests between the printed composite filament and porcine jaw bone. The samples were tested until failure or complete rupture at the interface. A trend was observed that as HAp content increased the adhesion stress between the porcine jaw bone and the composite filament increased (FIG. 3C). The ultimate adhesion stress increases from 30% (w/w) (216±43 kPa) to 40% (297±51 kPa) (FIG. 3C). These values were significantly higher than the control group of the PCL filament. We also took the images of the bone-material interface after adhesion test, which implies that there was no noticeable chemical interaction between the printed composite scaffold and bone tissue (FIG. 3D).

Filament Preparation and Printability Assessment

Figure 4A:
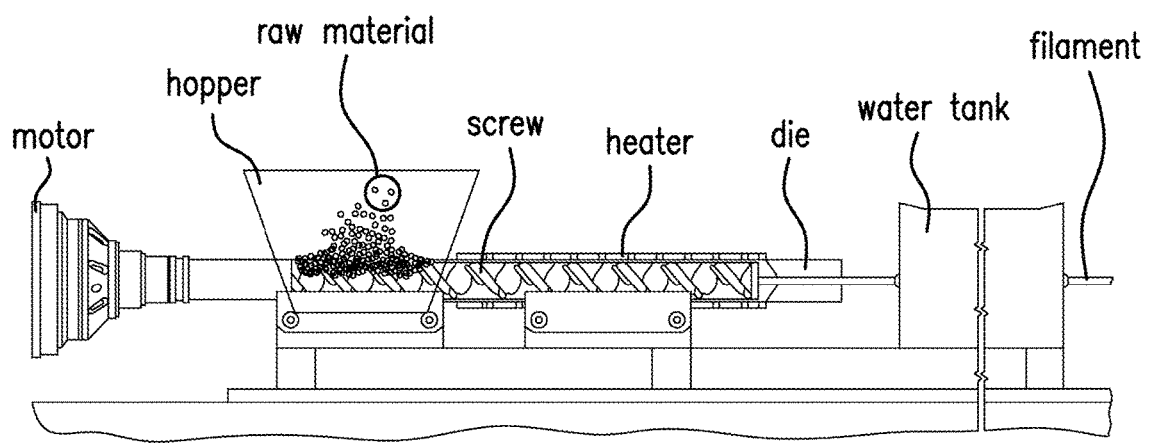
Figure 4B:
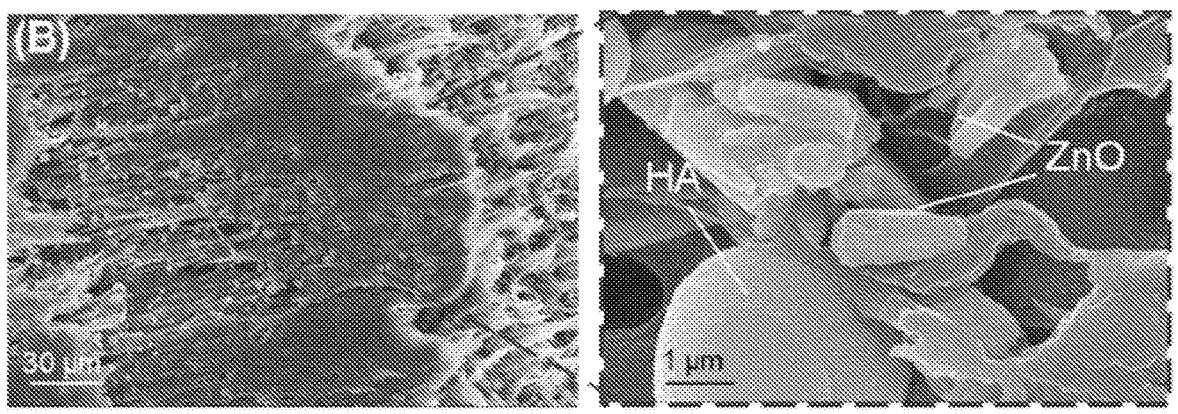

ZnO nanoparticles and HAp microparticles were incorporated into PCL to form uniform mixtures prior to extrusion. A custom-built filament extrusion device was used for extrusion of filaments with desired diameters (FIG. 4A). The composites were molten and then extruded through the 1.75 mm nozzle. A water-cooled reservoir located next to the extrusion nozzle quickly cooled down the extruded materials to form filaments. As a result, it was possible to make printable filaments using very little amounts of the materials (e.g. 10-20 g). Scanning electron microscopy (SEM) images of composite filaments confirmed the uniform distribution of ZnO nanoparticles and HAp microparticles throughout the fabricated composite filaments (FIG. 4B).

A schematic illustration of the filament preparation process is shown in FIG. 4C. Filaments with a diameter of 1.75 mm were easily loaded into commercially available handheld and stationary used filament fabrication printers (AIO Robotics 3D printing pen). Moreover, an integrated camera allowed for "on-the-fly" inspection of the printing quality (FIG. 4C). Several defects, 5 to 20 mm in diameter and with depths of 5 to 30 mm were created on a fresh porcine jaw bone and filled with printed scaffolds of the composite filament (FIG. 4D). This exhibited the handheld melt spun 3D printer's capability of producing scaffolds in hard to access areas and for irregular shaped defects. The printing quality of the composites was examined by printing a two-layer structure (35×35 mm) (FIG. 4E) which showed smoother printed lines in pristine PCL in comparison to PZH1 and PZH2.

Heat transfer from the printed filament onto the porcine jaw bone and an uninjured human hand was analyzed using a handheld thermal imaging system. The printing temperature of the tip of the pen was approximately 62° C. and the filament cooled within 9 s to 30° C. when printed on a human hand (FIG. 4F). The thermal transfer, while printing ex vivo bone defects, was also examined. The printing temperature was approximately 67° C. when filling a 12 mm deep defect in a fresh porcine jaw bone and cooled to 38° C. over a 28 s time period (FIG. 4D). The surrounding bone temperature did not rise above 40° C. during the printing process, which is expected not to be harmful to neighboring endogenous tissue.

Biological Characterization of the Scaffolds In Vitro

The antimicrobial activity of the printed scaffolds was demonstrated against a gram-positive bacteria Methicillin-resistant *Staphylococcus aureus* (MRSA), which is the most common cause of surgical infection, and can cause osteomyelitis (26, 27). After a 24 h incubation of printed scaffolds in tryptic soy broth (TSB) with 106 colony forming units (CFU)/ml of MRSA, the surface of the scaffolds was examined for the adherence of bacteria. SEM images (FIG. 5A) of the printed pristine PCL, together with the scaffolds incorporated with HAp and ZnO nanoparticles showed that the incorporation of 1% ZnO was highly effective against MRSA adhesion and proliferation onto the surface of the printed scaffolds compared to the control group. The results from the CFU assay indicated that the incorporation of ZnO nanoparticles could effectively inhibit the growth of MRSA on the surface of the printed scaffolds when compared to pristine PCL as the control group (FIG. 5B). Overall, significant differences were detected in the sensitivity of MRSA to the presence of ZnO nanoparticles.

Figure 5D:
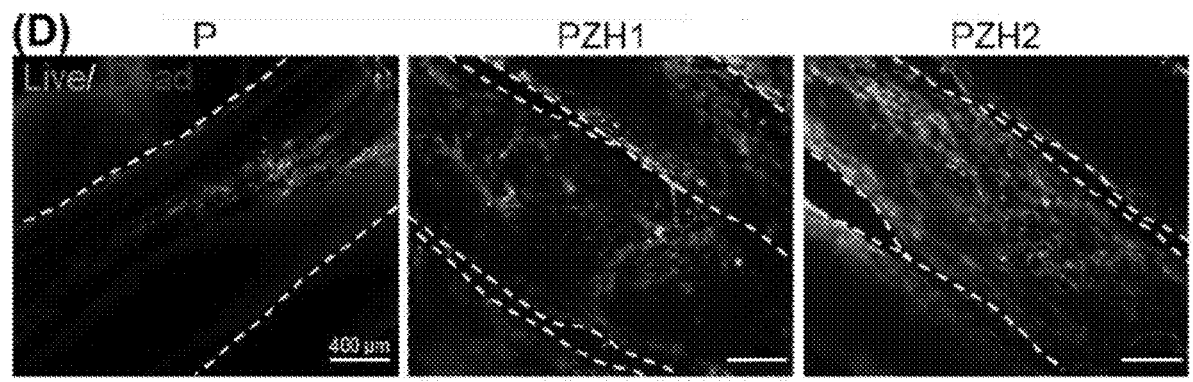

To demonstrate the interaction of cells and the printed composite scaffolds, human mesenchymal stem cells (hMSCs) were seeded on printed samples (10×10×2 mm). Potential cytotoxicity and the effect of scaffolds with different HAp concentrations on hMSCs proliferation were evaluated. Results from PrestoBlue™ Cell Viability Reagent on samples after days 1, 3, and 7 showed a gradual increase in metabolic activity, suggesting proliferation of cells. The proliferation rate was dependent upon the HAp concentration within the composition. For instance, the results indicated a significant difference of PZH2 samples (p<0.001 day 1, p<0.05 day 3) compared with the PCL specimens (FIG. 5C). Also, fluorescent microscopy images from Live/Dead staining (FIG. 5D) after 1 day of culture demonstrated that by increasing the HAp percentage in the material, live-cell density (green) increased and dead cell density (red) decreased.

Figure 6A:
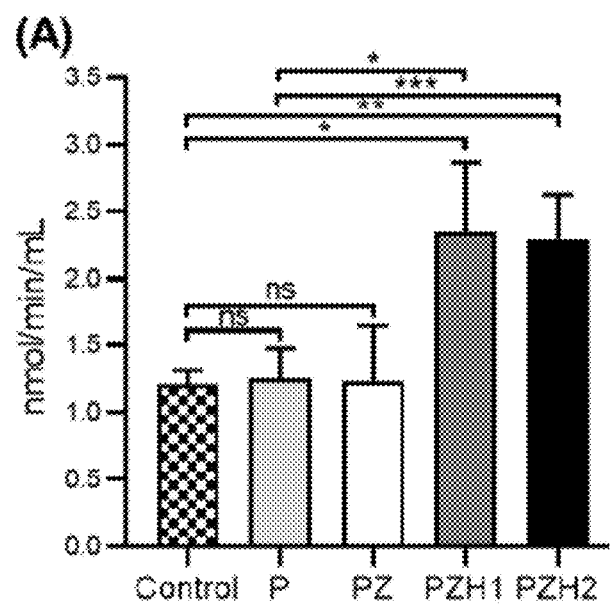
FIGS. 6A-C. In vitro assessment of osteogenic properties of printed scaffolds and osteodifferentiation evaluation of the cultured hMSCs. (A) ALP activity of the hMSCs on printed structures after culturing for 10 days (n=5). Composite samples containing HAp show significantly higher ALP activation in comparison to other groups. (B) Representative micrographs of immunostaining against osteopontin (OPN) as a late bone differentiation marker and nuclei (DAPI) at day 28 of culture indicating the differentiation of hMSCs to osteoblasts. The dashed lines indicate the borders of printed scaffolds. The results suggested that the confluency of cells and the intensity of markers were higher in groups with higher HAp concentration. (C) Confocal fluorescence images of xylenol orange staining of calcium deposition of differentiated cultured cells on composites at day 35 show significant improvement in cell mineralization by increasing the HAp in structures. Data are represented as mean±SD ($p<0.05$ (*), $p<0.01$(), $p<0.001$(*), ns (not significant), n=3).

The osteogenic properties of the printed scaffolds were demonstrated using hMSC. Alkaline phosphatase (ALP) activity assay was performed on seeded scaffolds after 10 days of culture providing an early differentiation marker for osteoblasts. The results (FIG. 6A) showed that the ALP activity was significantly higher in groups with HAp in comparison to 246 samples without HAp (PZH1 p≤0.05 and PZH2 p≤0.001) and cell control groups (PZH1 247 p≤0.05 and PZH2 p≤0.01).

Figure 6B:
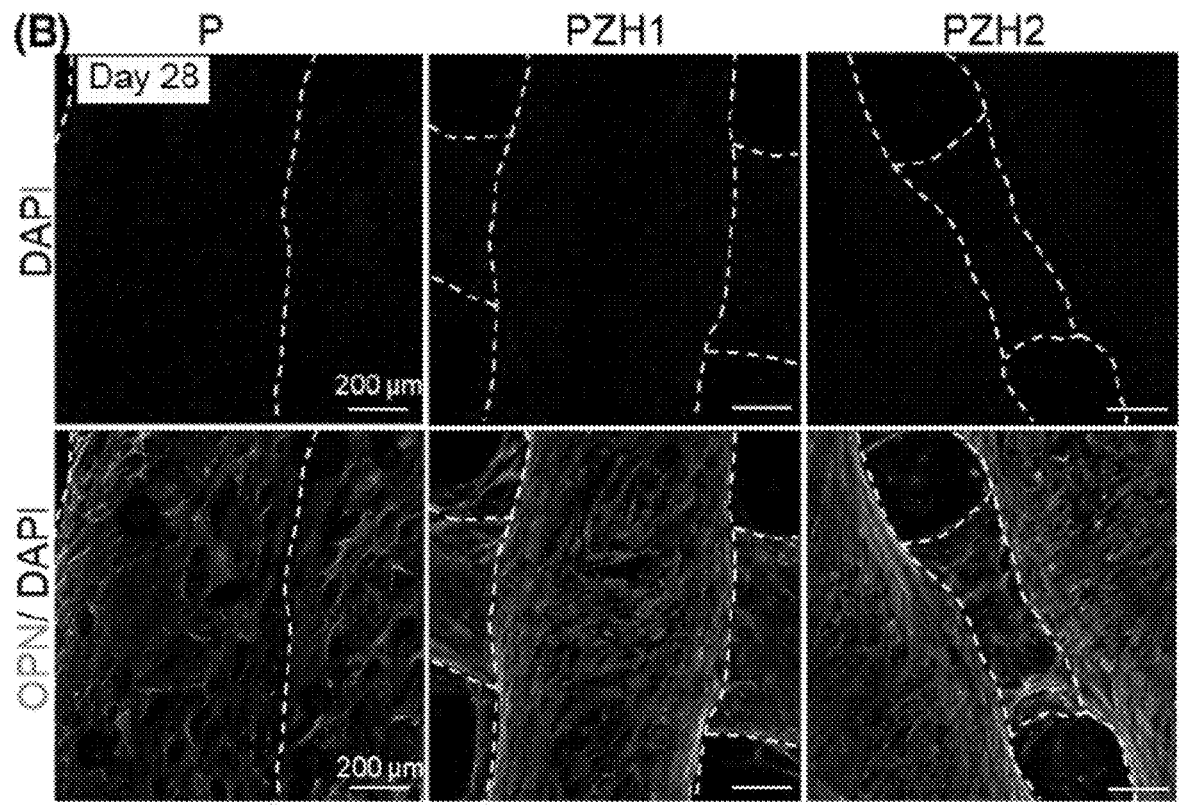

To confirm the osteodifferentiation of hMSCs, the expression of RUNX2 and collagen I as earlier (day 21) and osteopontin (OPN) (FIG. 6B) and bone sialoprotein (BSP) 250 as later (day 28) osteogenic markers of the cultured cells were assessed. The micrographs of immunostained cultured hMSC confirmed that the majority of cells expressed osteodifferentiation markers, suggesting the osteogenic maturation of hMSCs. Moreover, the confluency of differentiated cells increased from the pristine PCL to PZH2 sample.

Figure 6C:
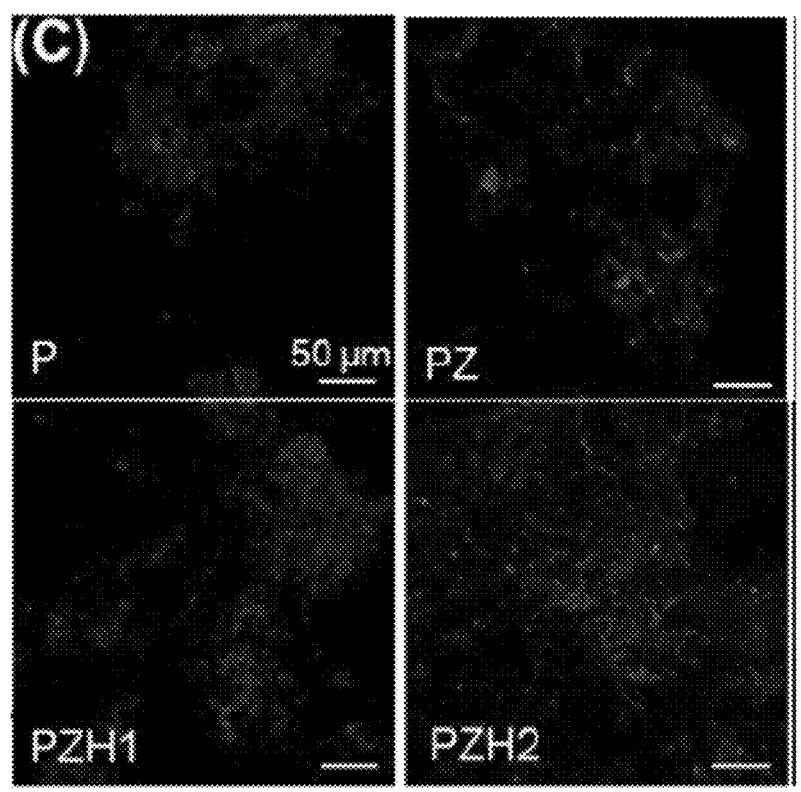

To further evaluate the osteodifferentiation of hMSCs and their functional mineralization, xylenol orange staining was performed to assess the de novo calcium deposition of the differentiated cells. Xylenol orange is a fluorochromatic calcium-chelating dye (red fluorescence) which only binds to newly formed mineralized extracellular matrix which allows one to distinguish them from the present minerals in HAp used for scaffold fabrication (28, 29). The results confirmed remarkably higher calcium deposition by differentiated cells on printed scaffolds as a function of increasing HAp concentration (FIG. 6C).

Animal Study

Figure 7A:
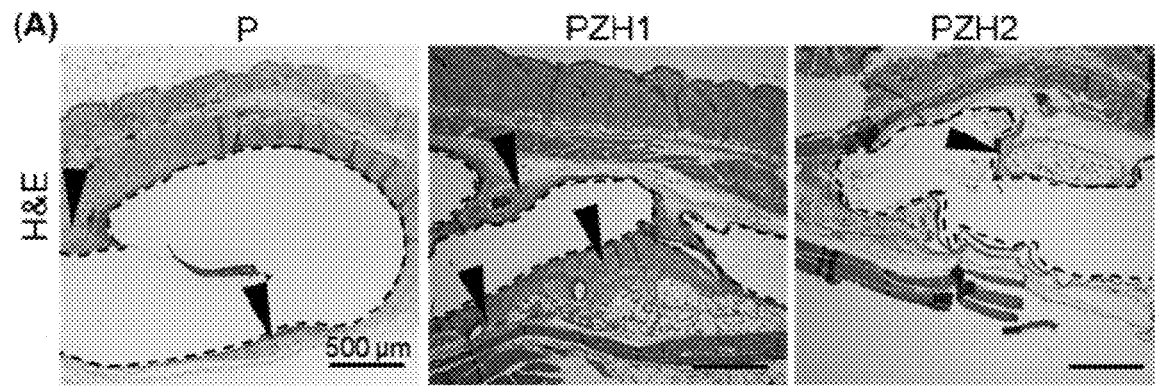
FIGS. 7A-D. Histological assessment of tissue reaction to in situ printed structure after subcutaneous implantation in mice after 4 weeks. (A, B) Hematoxylin and eosin (H&E) and Masson's trichrome (MT) staining of the interface of subcutaneous tissue around the printed filaments. The arrows represent the regions of fibrosis. (C, D) Immunohistofluorescence staining against CD68 and CD31 which are markers for macrophages and endothelial cells, respectively. The arrows represent the macrophages and new small vessels in C and D rows, respectively. Dashed lines indicate the scaffold-tissue interfaces. (n=6).
Figure 7B:
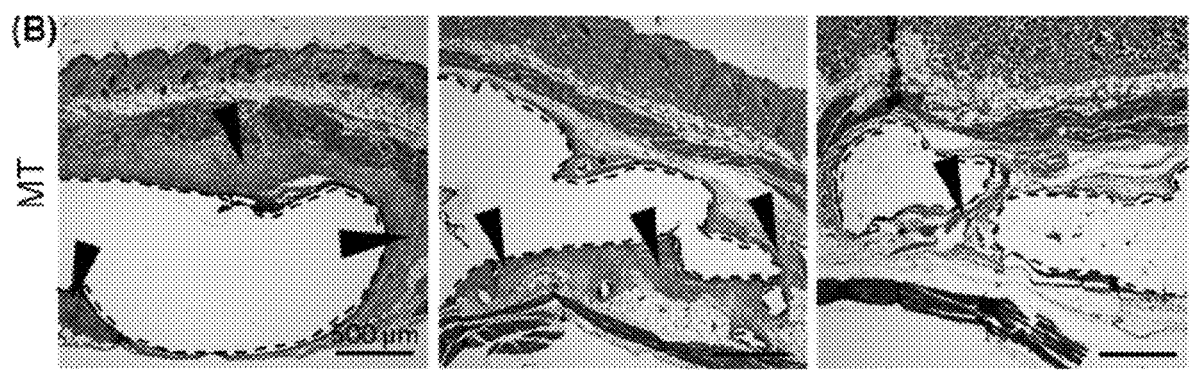

To evaluate the biocompatibility and the host response to the in situ printed scaffolds, materials were directly implanted in a subcutaneous pocket in the dorsum of mice. Animals were divided into three study groups: 1) animals with in situ printed scaffolds of pristine PCL scaffolds; 2) animals with in situ printed scaffolds of PZH1; and 3) animals with in situ printed scaffolds of PZH2 (n=6, n=samples replicate of each group at each time point). The animals were monitored every other day and no severe inflammation or edema was observed at the implantation site. All the animals survived the surgery and no abnormal eating habit or weight loss was observed throughout the duration of the experiment in all tested animals. Animals were sacrificed at two time points of day 7 and 28 post surgery to assess early and chronic inflammation. Post-euthanization, the samples and the surrounding tissues were harvested and characterized by histological analysis. Histological micrographs of the samples harvested on day 7 and 28 post surgery are shown in FIG. 7A-7D. The hematoxylin and eosin (H&E) stained slides showed that the tissue surrounding samples of PZH1 and PZH2 contained less inflammatory cells than the PCL samples, which were identified as neutrophils and macrophages when viewed at a 400× magnification. Masson's trichrome (MT) staining also was compatible with a smaller thickness and decreased density of fibrosis around the PZH1 and PZH2 scaffolds (FIG. 7B).

Figure 7C:
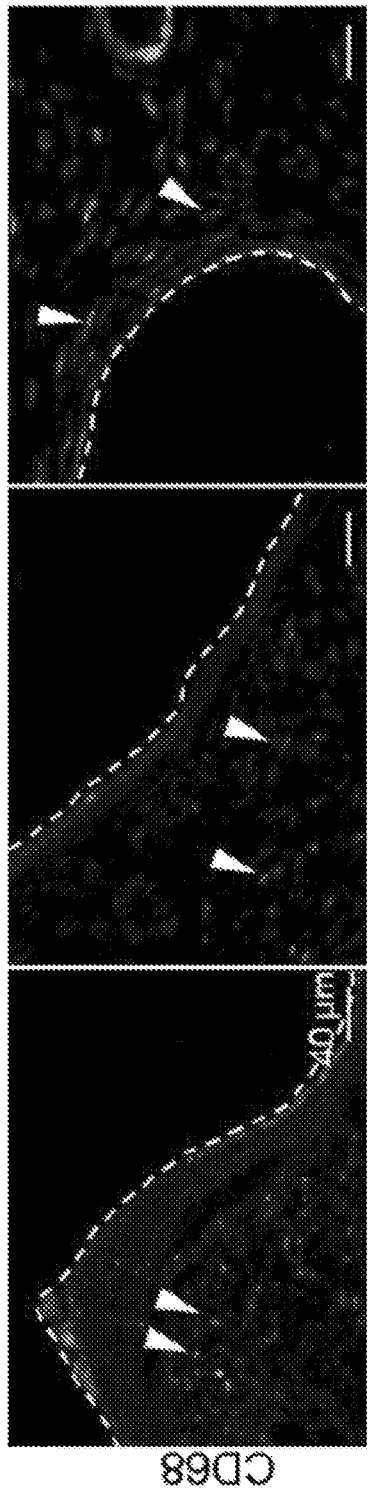
Figure 7D:
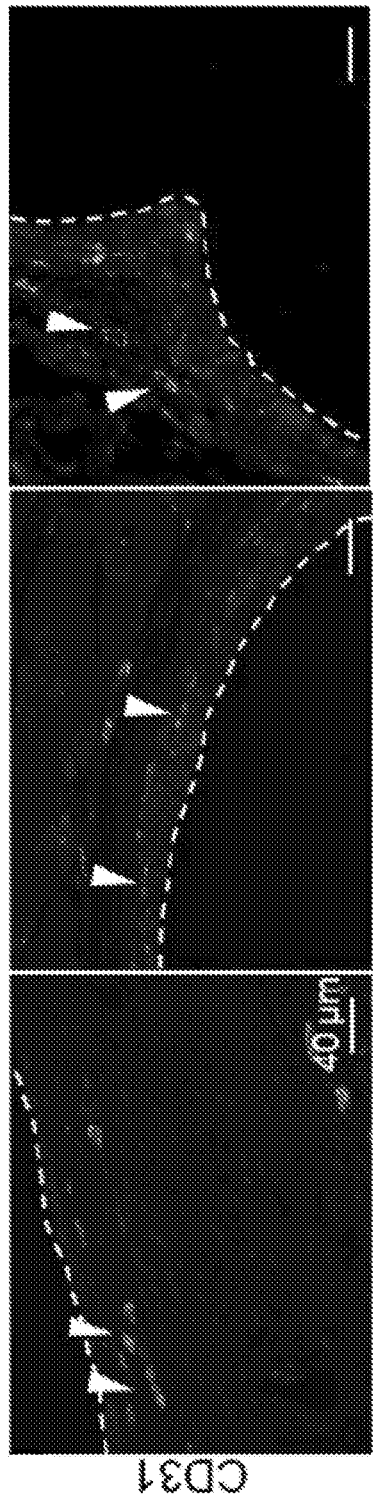

Immunostaining against macrophages (CD68; FIG. 7C) showed a slight inflammatory response, which is in the normal range for implanted synthetic materials. However, the number of CD68 positive cells in PZH1 and PZH2 scaffolds were overall less than those observed in pristine PCL scaffolds. The rate of vascularization at the interface of the samples was investigated by immunostaining against CD31, expressed by endothelial cells (FIG. 7D). The results suggested the presence of more capillaries at the interface of PZH1 and PZH2 scaffolds.

DISCUSSION 3D printing and bioprinting have emerged as promising strategies for creating biomimetic architectures to repair, replace or regenerate damaged tissues (20, 30). The use of 3D printed polymeric scaffolds has especially been popular for engineering both cell-laden and acellular bone grafts (19, 20, 31). However, one challenge is that bone defects are typically irregular in shape and as a result, printing structures that can fit the defect site is not trivial. Additionally, in conventional surgical procedures, the scaffolds need to be fixed either through suturing or the use of surgical glues and cements at their interface with the surrounding tissues (17). For instance, one of the most commonly used cements in clinical applications is poly(methyl methacrylate), or PMMA which has a highly exothermic (around 80° C.) polymerization reaction in situ resulting in damage of the surrounding bone tissue (32). The use of such materials at tissue interfaces can significantly alter the therapeutic outcome. One potential solution to overcome these challenges is to directly create the scaffold in situ and in vivo (i.e; within the patient's body). This strategy has been successfully used for the treatment of injuries in soft tissues such as skeletal muscles and skin (33). To the best of our knowledge, this is the first time in situ printing of composite polymeric systems that offer mechanical properties comparable to hard tissues was applied. This handheld printer is capable of extruding materials at different rates, where the printing quality can be controlled by the flow rate, moving speed, and moving direction. This eliminates the complexities associated with the presence of 3D scanning and computational facility. The resolution can be improved through the use of noise canceling devices.

The local increase of the surrounding tissue temperature is an important concern to consider when selecting the printable materials. Here, the low melting temperature of PCL-based composites enabled the in situ printing of clinically relevant sized scaffolds without increasing the local temperature to >40° C. The composition did not show any immune reaction with the host tissues, and the mechanical interlock and penetration of the scaffolding material within the small cavities led to sufficient adhesion to avoid scaffold slipping or dislocation during the surgical procedure. It also showed the handheld printing resolution and the possibility of creating proper pores in the structure that could support cell infiltration and bone regeneration. Meanwhile, we also considered the impact of bacterial infection during the surgical treatment, which could cause osteomyelitis (i.e. a life-threatening disease, and 20-30% of treatments end in failure) (27). In order to avoid such circumstances, we introduced highly effective antibacterial ZnO nanoparticles into the printable composite scaffolds.

The successful implementation of any scaffolding system in regenerative medicine depends on its biocompatibility, suitable physicochemical properties, degradation rate, and its interaction with relevant cell types. The growth of new bone tissue is a dawdling process, and a slower degradation is expected to ensure biomechanical stability of PCL-based constructs prior to tissue remodeling (19). Our result suggests that the degradation rate of PCL-based composite filaments can be further slowed down by changing the mass percentage of HAp in the composite.

Adhesion of scaffolds to the defect site's surrounding tissue is another important factor for the healing process, as they must maintain their integrity while tissue ingrowth and regeneration occurs (34). The scaffold must remain mechanically stable and not induce stress shielding around the implant site (34). Furthermore, the mechanical strength of the developed scaffolds was comparable to the values for some of the bone tissues such as alveolar and cancellous bones (35, 36). While there is a significant mismatch with some of the load bearing bones, upon further optimization of the composite scaffolds, it appears feasible that this strategy could be applied for the treatment of defects within load bearing bones (30). As shown, the mechanical strength of the composite scaffolds is approximately in the range of 24~28 MPa, where the numbers for cancellous bones are 4-70 MPa (36). Similarly, 265~280 MPa of elastic moduli could be obtained for the composite scaffolds, which are in the range of maxillofacial and cranial tissues (20-500 MPa) (37).

The biocompatibility of the scaffolds was assessed both in vitro and in vivo. In vitro, hMSCs were seeded on the scaffolds and their viability and metabolic activity were assessed. MSCs are an important cell population contributing to bone regeneration, and scaffolds utilized for the treatment of bone defects should be able to support their growth and differentiation. The viability ratio and the growth curve of the cultured MSCs were comparable to the control groups cultured in tissue culture plates suggesting a lack of toxicity of the scaffolding materials. In addition, it was observed that combining PCL and HAp improved cellular attachment and proliferation, especially at the initial stage (days 1 and 3). This is in agreement with the changes in the contact angle and protein absorption of scaffolds containing HAp. The changes in the filaments surface topography might also be another contributing factor in improving the interaction of cells and the composite scaffolds. A similar observation was reported in other studies (21, 38).

The osteogenic potential of composite scaffolds was assessed by monitoring the cultured hMSCs over time and different levels of cellular activities. The expression of ALP as an early marker for osteoblast differentiation and functionality was measured through ALP activity assay. ALP enzyme produced by osteodifferentiating cells is essential to bone regeneration because it catalyzes inorganic phosphate generation, which is a key substrate for mineralization and HAp formation. A higher level of ALP activities was observed in cells cultured on composite scaffolds containing HAp in comparison to pure PCL. This result suggested that composite scaffolds better supported the osteodifferentiation of cultured cells. It has also been reported that HAp positively stimulates osteoblastic cellular activity (39, 40). Furthermore, the micrographs of immunostained hMSC cultured at different time points confirmed their differentiation to osteoblasts and revealed that the concentration of proteins and cell confluency increased by adding HAp to the composites. This suggests that HAp containing composites provided a better substrate for cellular anchorage, proliferation, and differentiation.

The biocompatibility of the scaffolding materials and the in situ printing approach were further assessed by their implantation in a subcutaneous pocket in wild type mice. Histology results showed that incorporation of HAp and ZnO lowered the inflammation level of PCL, even though the range of inflammation response of all the samples was not high and would be expected for a sterile implant. Subcutaneous implantation is suitable for understanding the extent of support a scaffold offers for vascularization. The number of new blood vessels formed in tissues around the material was higher in groups with HAp, specially PZH2 than pure PCL. Thus, the in situ printed porous scaffolds within a bone defect can support cell infiltration and vascularization.

Overall, the present in situ printed PCL based composite scaffold provides a simple but effective surgical platform to fix critically large bone defects, and facilitate bone tissue regeneration. Current composite materials are clearly osteoconductive. Through incorporation of osteogenic factors and compounds, the in situ printed scaffolds can be rendered osteoinductive.

EXEMPLARY CONCLUSIONS

In this Example, for the first time, we introduced the in situ printing of nanoengineered hard polymeric scaffolds for the treatment of bone defects. Filaments from PCL, HAp, and ZnO nanoparticles were fabricated using a custom-built extrusion setup which enabled us to create several meters of these filaments rapidly. The material composition and its homogeneity were confirmed using various techniques. The addition of HAp reduced the hydrophobicity of the composition and improved the protein absorption. The filaments were then extruded using a handheld printer. The in situ printing of the filaments resulted in reasonable adhesion of the scaffolds to the surrounding tissues without increasing their local temperature to >40° C. The biocompatibility of the scaffolds was tested in vitro by culturing hMSCs in vivo upon their in situ printing in a subcutaneous pocket in wild type mice. The scaffolds supported the growth and proliferation, as well as the osteodifferentiation of hMSCs. The incorporated ZnO particle inhibited the growth of bacteria on the surface of scaffolds which is important for the treatment of traumatic injuries. This is a paradigm shift in the treatment of bone defects. Furthermore, the invention can easily be extended for the delivery of biological materials, such as cells, growth factors, and autografts into bone defects.

Acknowledgment

The authors extend their appreciation to the Deputyship for Research & Innovation, Ministry of Education in Saudi Arabia for funding this research work through the project number IFPRC-005-135-2020 and King Abdulaziz University, DSR, Jeddah, Saudi Arabia.

REFERENCES

1. E. H. Schemitsch, Size matters: defining critical in bone defect size! *Journal of orthopaedic trauma* 31, S20-S22 (2017).
2. E. Alsberg, E. E. Hill, D. J. Mooney, Craniofacial tissue engineering. *Crit. Rev. Oral Biol. Med.* 12, 64-75 (2001).
3. G. Calori, E. Mazza, M. Colombo, C. Ripamonti, The use of bone-graft substitutes in large bone defects: any specific needs? *Injury* 42, S56-S63 (2011).
4. R. Murugan, S. Ramakrishna, Development of nanocomposites for bone grafting. *Composites Science and Technology* 65, 2385-2406 (2005).
5. J. A. Buza, 3rd, T. Einhorn, Bone healing in 2016. *Clin Cases Miner Bone Metab* 13, 101-105 (2016).
6. E. Gómez-Barrena et al., Feasibility and safety of treating non-unions in tibia, femur and humerus with autologous, expanded, bone marrow-derived mesenchymal stromal cells associated with biphasic calcium phosphate biomaterials in a multicentric, non-comparative trial. *Biomaterials*, (2018).
7. P. V. Giannoudis, H. Dinopoulos, E. Tsiridis, Bone substitutes: an update. *Injury* 36, S20-S27 (2005).
8. M. Farrington, I. Matthews, J. Foreman, K. M. Richardson, E. Caffrey, Microbiological monitoring of bone grafts: two years' experience at a tissue bank. *Journal of Hospital Infection* 38, 261-271 (1998).
9. P. Habibovic, K. de Groot, Osteoinductive biomaterials—properties and relevance in bone repair. *Journal of tissue engineering and regenerative medicine* 1, 25-32 (2007).
10. M. Á. Brennan et al., Pre-clinical studies of bone regeneration with human bone marrow stromal cells and biphasic calcium phosphate. *Stem cell research & therapy* 5, 114 (2014).
11. A. S. Herford, M. Miller, F. Signorino, Maxillofacial Defects and the Use of Growth Factors. *Oral Maxillofac Surg Clin North Am* 29, 75-88 (2017).
12. T. Dvir, B. P. Timko, D. S. Kohane, R. Langer, Nanotechnological strategies for engineering complex tissues. *Nature nanotechnology* 6, 13 (2011).
13. S. Bose, S. Vahabzadeh, A. Bandyopadhyay, Bone tissue engineering using 3D printing. *Materials today* 16, 496-504 (2013).
14. H.-W. Kang et al., A 3D bioprinting system to produce human-scale tissue constructs with structural integrity. *Nature biotechnology* 34, 312 (2016).
15. S. Wu, B. Duan, X. Qin, J. T. Butcher, Living nano-micro fibrous woven fabric/hydrogel composite scaffolds for heart valve engineering. *Acta Biomaterialia* 51, 89-100 (2017).
16. M. Akbari et al., Composite Living Fibers for Creating Tissue Constructs Using Textile Techniques. *Advanced Functional Materials* 24, 4060-4067 (2014).
17. C. S. Russell et al., In Situ Printing of Adhesive Hydrogel Scaffolds for the Treatment of Skeletal Muscle Injuries. *ACS Applied Bio Materials* 3, 1568-1579 (2020).
18. Y. K. Mishra, R. Adelung, ZnO tetrapod materials for functional applications. *Materials Today* 21, 631-651 (2018).
19. Z.-Z. Zhang et al., Orchestrated biomechanical, structural, and biochemical stimuli for engineering anisotropic meniscus. *Science translational medicine* 11, eaao0750 (2019).
20. A. E. Jakus et al., Hyperelastic "bone": A highly versatile, growth factor—free, osteoregenerative, scalable, and surgically friendly biomaterial. *Science translational medicine* 8, 358ra127-358ra127 (2016).
21. S. Gerdes et al., Process-Structure-Quality Relationships of Three-Dimensional Printed Poly (Caprolactone)-Hydroxyapatite Scaffolds. *Tissue Engineering Part A*, (2020).
22. X. Li, Q. Zou, H. Chen, W. Li, In vivo changes of nanoapatite crystals during bone reconstruction and the differences with native bone apatite. *Science advances* 5, eaay6484 (2019).
23. N. Salah et al., Size controlled, antimicrobial ZnO nanostructures produced by the microwave assisted route. *Materials Science and Engineering: C* 99, 1164-1173 (2019).
24. A. Nasajpour et al., Nanostructured Fibrous Membranes with Rose Spike-Like Architecture. *Nano Letters* 17, 6235-6240 (2017).
25. D. Wu, Y. Zhang, M. Zhang, W. Yu, Selective localization of multiwalled carbon nanotubes in poly (ε-caprolactone)/polylactide blend. *Biomacromolecules* 10, 417-424 (2009).
26. E. E. West, R. Spolski, M. Kazemian, C. Kemper, W. J. Leonard, A TSLP-complement axis mediates neutrophil killing of methicillin-resistant *Staphylococcus aureus*. *Science immunology* 1, (2016).
27. E. J. Ryan et al., Collagen scaffolds functionalised with copper-eluting bioactive glass reduce infection and enhance osteogenesis and angiogenesis both in vitro and in vivo. *Biomaterials* 197, 405-416 (2019).
28. R. Shu, R. McMullen, M. Baumann, L. McCabe, Hydroxyapatite accelerates differentiation and suppresses growth of MC3T3-E1 osteoblasts. *Journal of Biomedical*

Materials Research Part A: An Official Journal of The Society for Biomaterials, The Japanese Society for Biomaterials, and The Australian Society for Biomaterials and the Korean Society for Biomaterials 67, 1196-1204 (2003).
29. B. A. Rahn, S. M. Perren, Xylenol orange, a fluorochrome useful in polychrome sequential labeling of calcifying tissues. *Stain Technology* 46, 125-129 (1971).
30. M. Zhang et al., 3D printing of Haversian bone-mimicking scaffolds for multicellular delivery in bone regeneration. *Science Advances* 6, eaaz6725 (2020).
31. A. Nasajpour et al., A multifunctional polymeric periodontal membrane with osteogenic and antibacterial characteristics. *Advanced Functional Materials* 28, 1703437 (2018).
32. A. Ricker, P. Liu-Snyder, T. J. Webster, The influence of nano MgO and BaSO4 particle size additives on properties of PMMA bone cement. *International journal of nanomedicine* 3, 125 (2008).
33. K. Ma et al., Application of robotic-assisted in situ 3D printing in cartilage regeneration with HAMA hydrogel: An in vivo study. *Journal of Advanced Research* 23, 123-132 (2020).
34. M. M. Hasani-Sadrabadi et al., An engineered cell-laden adhesive hydrogel promotes craniofacial bone tissue regeneration in rats. *Science Translational Medicine* 12, (2020).
35. S. Subramaniam, Y.-H. Fang, S. Sivasubramanian, F.-H. Lin, C.-p. Lin, Hydroxyapatite-calcium sulfate-hyaluronic acid composite encapsulated with collagenase as bone substitute for alveolar bone regeneration. *Biomaterials* 74, 99-108 (2016).
36. Y. Li et al., Novel β-Ti35Zr28Nb alloy scaffolds manufactured using selective laser melting for bone implant applications. *Acta biomaterialia* 87, 273-284 (2019).
37. S. M. Kurtz, *PEEK biomaterials handbook.* (William Andrew, 2019).
38. H. J. Lee et al., The effect of surface-modified nanohydroxyapatite on biocompatibility of poly (ϵ-caprolactone)/hydroxyapatite nanocomposites. *European Polymer Journal* 43, 1602-1608 (2007).
39. L. Shor, S. Güçeri, X. Wen, M. Gandhi, W. Sun, Fabrication of three-dimensional polycaprolactone/hydroxyapatite tissue scaffolds and osteoblast-scaffold interactions in vitro. *Biomaterials* 28, 5291-5297 (2007).
40. Z. Wang et al., Nanocalcium-deficient hydroxyapatite-poly (ϵ-caprolactone)-polyethylene glycol-poly (ϵ-caprolactone) composite scaffolds. *International journal of nanomedicine* 7, 3123 (2012).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. A method of treating a bone defect or injury or reconstructing a new bone for cosmetic or non-cosmetic purposes in a subject in need thereof, comprising:
    using a handheld 3D printer to directly deposit a filament or printing material into the bone defect of the subject, wherein the filament or printing material comprises a polymer having a melting point of 70° C. or lower, wherein the filament or printing material comprises polycaprolactone, zinc oxide particles, and hydroxyapatite particles; and
    monitoring the application of the composite filament using a camera, and
    wherein the handheld 3D printer comprises:
        a housing defining a proximal end and a distal end opposite the proximal end, the housing including a receptacle for receiving a portion of a syringe or a filament assembly within the housing;
        a power supply disposed within the housing;
        an electric actuator disposed within the housing at a position sufficient to facilitate an operable coupling of the electric actuator to at least a portion of a plunger of the syringe or filament assembly upon an insertion into the receptacle;
        a control interface positioned at least partially within the housing and including at least one control device operable from an exterior of the housing;
        a controller disposed within the housing and coupled to the power supply, the electric actuator, and the control interface;
        a heater that heats up at least part of the syringe or the filament upon an insertion into the receptacle, the controller configured to regulate a flow of power from the power supply to the electric actuator and heater based on signals received from the at least one control device to facilitate regulating an actuation of the plunger by the electric actuator; and
        a heated nozzle with a size or geometry that allows extrusion of the filament out of the printer.

2. The method of claim 1, wherein the method is performed as part of a neurosurgical craniotomy, a craniomaxillofacial (CMF) surgery reconstruction, reconstruction of extremities, an adult or pediatric orthopedic surgery, treatment of a facial fracture, or a spinal surgery.

3. The method of claim 1, wherein the filament or printing material further comprises at least one of an antimicrobial agent, osteoconductive agent, and a protein.

4. The method of claim 1, wherein the filament or printing material further comprises at least one of a metal, metal oxide, mineral, bioglass, small molecule drug, radiopaque agent, antibacterial compound, antibiotic, bioceramic, ceramic, oxygen generating material, crosslinking agent, vitamin, lipid, phospholipid, fatty acid, salt, biological factor, polysaccharide, nucleic acid, growth factor, hydroxyapatite, calcium phosphate, carbon nanotube, quaternary ammonium compound, graphene, graphene oxide, carbon derived material, liquid crystal, peptide, chitosan, alginate, silver nitride, platelet rich plasma, a blood derived material, bone marrow derived materials, pain killers, anti-inflammatory drugs or reagents, and hydrogen peroxide.

5. The method of claim 1, wherein the camera is attached to the handheld 3D printer.

6. The method of claim 1, wherein the bone defect has a nominal diameter greater than 0.2 mm and has a depth of greater that 0.2 mm.

7. The method of claim 1, wherein the bone defect has an irregular shape and/or involves multiples tissues.

8. A method of fixing, adhering, or gluing a bone fracture, a bone flap, a bone graft and/or pieces of bone in a subject in need thereof, comprising:
    imaging the bone fracture, bone flap, or bone graft and/or at an interface of a flap and a bone within the subject; and
    while imaging, using a handheld 3D printer to directly deposit a filament or printing material inside, over and/or around the bone fracture, bone flap, or bone graft and/or at an interface of a flap and a bone within the subject, wherein the filament or printing material comprises a polymer having a melting point of 70° C. or lower, wherein the handheld 3D printer comprises:
- a housing defining a proximal end and a distal end opposite the proximal end, the housing including a receptacle for receiving a portion of a syringe or a filament assembly within the housing;
- a power supply disposed within the housing;
- an electric actuator disposed within the housing at a position sufficient to facilitate an operable coupling of the electric actuator to at least a portion of a plunger of the syringe or filament assembly upon an insertion into the receptacle;
- a control interface positioned at least partially within the housing and including at least one control device operable from an exterior of the housing;
- a controller disposed within the housing and coupled to the power supply, the electric actuator, and the control interface;
- a heater that heats up at least part of the syringe or the filament upon an insertion into the receptacle, the controller configured to regulate a flow of power from the power supply to the electric actuator and heater based on signals received from the at least one control device to facilitate regulating an actuation of the plunger by the electric actuator; and
- a heated nozzle with a size or geometry that allows extrusion of the filament out of the printer.

9. The method of claim 8, wherein the filament or printing material is used without fracture fixation devices or additional bone grafts.

10. The method of claim 8, wherein the filament or printing material further comprises at least one of an antimicrobial agent, osteoconductive agent, and a protein.

11. The method of claim 8, wherein the filament or printing material comprises one or more of functionalized or non-functionalized polycaprolactone (PCL), polylactic acid, polyglycolic acid, poly(L-lactide-co-ϵ-caprolactone), poly(ethylene adipate), poly(ethylene oxide), polyethylene co methacrylic acids, poly(tetramethylene oxide) (PTMO), collagen, and gelatin.

12. The method of claim 8, wherein the filament or printing material further comprises at least one of a metal, metal oxide, bioglass, small molecule drug, radiopaque agent, antibacterial compound, antibiotic, bioceramic, ceramic, oxygen generating material, crosslinking agent, vitamin, lipid, phospholipid, fatty acid, salt, biological factor, polysaccharide, nucleic acid, growth factor, hydroxyapatite, calcium phosphate, carbon nanotube, quaternary ammonium compound, graphene, graphene oxide, carbon derived material, liquid crystal, peptide, chitosan, alginate, silver nitride, platelet rich plasma, a blood derived material, anti-inflammatory drugs or reagents, and hydrogen peroxide.

13. The method of claim 8 wherein the camera is attached to the handheld 3D printer.

14. A method for retaining a bone graft and/or a bone graft substitute in a bone defect of a subject, comprising:
- placing the bone graft and/or the bone graft substitute in a specific location at the bone defect of the subject;
- using a handheld 3D printer to directly deposit printing material from a filament at the bone defect of the subject, wherein the printing material comprises a polymer having a melting point of 70° C. or lower, wherein the printing material is deposited so as to print in situ a graft cage at the defect, wherein the graft cage is sized to retain the bone graft and/or bone graft substitute in the specific location in the defect; and
- allowing said subject to heal while said bone graft and/or bone graft substitute is retained at the specific location using the graft cage.

15. The method of claim 14 wherein said printing material comprises polycaprolactone (PCL), zinc oxide particles, and hydroxyapatite particles.

16. The method of claim 14 wherein said graft cage is absorbed by subject during healing.

17. The method of claim 14 wherein using the handheld 3D printer is accompanied by monitoring the application of the printing material using a camera attached to the handheld 3D printer.

18. The method of claim 14 wherein the handheld 3D printer comprises:
- a housing defining a proximal end and a distal end opposite the proximal end, the housing including a receptacle for receiving a portion of a syringe or a filament assembly within the housing;
- a power supply disposed within the housing;
- an electric actuator disposed within the housing at a position sufficient to facilitate an operable coupling of the electric actuator to at least a portion of a plunger of the syringe or filament assembly upon an insertion into the receptacle;
- a control interface positioned at least partially within the housing and including at least one control device operable from an exterior of the housing;
- a controller disposed within the housing and coupled to the power supply, the electric actuator, and the control interface;
- a heater that heats up at least part of the syringe or the filament upon an insertion into the receptacle, the controller configured to regulate a flow of power from the power supply to the electric actuator and heater based on signals received from the at least one control device to facilitate regulating an actuation of the plunger by the electric actuator; and
- a heated nozzle with a size or geometry that allows extrusion of the filament out of the printer.

* * * * *